US 6,806,075 B1
United States Patent
Morser et al.
Patent No.: US 6,806,075 B1
Date of Patent: Oct. 19, 2004

(54) CORIN, A SERINE PROTEASE

(75) Inventors: John Michael Morser, San Francisco, CA (US); Qingyu Wu, El Sorbante, CA (US); Wei Yan, Hercules, CA (US)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/959,392

(22) PCT Filed: Jun. 4, 1999

(86) PCT No.: PCT/EP99/03895

§ 371 (c)(1),
(2), (4) Date: Jun. 25, 2002

(87) PCT Pub. No.: WO99/64608

PCT Pub. Date: Dec. 16, 1999

Related U.S. Application Data

(60) Provisional application No. 60/367,347, filed on Jun. 5, 1998, and provisional application No. 60/219,329, filed on May 20, 1999.

(51) Int. Cl.[7] .......................... C12N 9/64; C12N 15/57; C12N 15/79; C12N 15/85; C12Q 1/37
(52) U.S. Cl. ...................... 435/226; 435/23; 435/69.1; 435/252.3; 435/320.1; 536/23.2
(58) Field of Search .................. 435/226, 23, 69.1, 435/252.3, 320.1; 536/23.2

(56) References Cited

U.S. PATENT DOCUMENTS

| | | | |
|---|---|---|---|
| 5,869,637 A | | 2/1999 | Au-Young et al. .......... 536/23.5 |
| 5,962,266 A | * | 10/1999 | White et al. ................ 435/69.2 |
| 6,479,274 B1 | * | 11/2002 | Antalis et al. ............. 435/252.3 |
| 2003/0073623 A1 | * | 4/2003 | Drmanac et al. ............. 514/12 |
| 2003/0092154 A1 | * | 5/2003 | Antalis et al. ............... 435/194 |
| 2003/0119168 A1 | * | 6/2003 | Madison et al. ............ 435/226 |

FOREIGN PATENT DOCUMENTS

| WO | WO 98 03665 A | 1/1998 |
|---|---|---|
| WO | WO 98 36054 A | 8/1998 |
| WO | WO 98 45436 A | 10/1998 |

OTHER PUBLICATIONS

Seffernick, J. L. et al., 2001. "Melamine deaminase and atrazine chlorohydrolase: 98 percent identical but functionally different", Journal of Biochemistry, vol. 183, pp. 2405–2410.*

W. Yan et al., "Corin, a Mosaic Transmembrane Serine Protease Encoded By A Novel cDNA from Human Heart," Database Medline (Online), U.S. National Library of Medicine (NLM), Bethesda, MD, XP002119684, Abstract & Journal of Biological Chemistry, May 21, 1999, vol. 274 (21) pp. 14926–35.

Y. Tomita et al., "A Novel Low–Density Lipoprotein Receptor–related Protein With Type II Membrane Protein–Like Structure is Abundant In Heart," Journal of Biochemistry, vol. 124, Oct. 1998, pp. 784–789, XP002119680, Japanese Biochemical Society, Tokyo, JP ISSN: 0021–924X.

EMBL/Genbank Databases, Accession No. AA 249210 Sequence Reference HS1163286, Liew C: "cDNAs from Human Fetal Heart," XP002119683.

(List continued on next page.)

Primary Examiner—Ponnathapura Achutamurthy
Assistant Examiner—William W. Moore
(74) Attorney, Agent, or Firm—Millen, White, Zelano & Branigan, P.C.

(57) ABSTRACT

The present invention relates to a corin polypeptide which contains one or more frizzled corin and possesses various activities, including, e.g., serin protease activity and a pro-ANF converting activity, LDLR, SRCR repeats, serine protease catalytic domains such as human and mouse corin. The invention further relates to methods of using such nucleic acids and polypeptides in therapeutics, diagnostics, and research. For example, the nucleic acids and polypeptides of corin can be utilized in methods to identify modulators of its activity, in animal models to mimic human disease, and to treat kidney, cardiovascular, and other conditions in which corin is involved.

17 Claims, 4 Drawing Sheets

Domain Structure of Human Corin Protein

- ◆ Transmembrane
- ▭ Frizzled cysteine-rich domain
- ● LDLR repeat
- ● Scavenger receptor-like repeat
- ■ Serine protease catalytic domain

OTHER PUBLICATIONS

EMBL/Genbank Databases Accession No. AA906367 Sequence Reference AA906367 Apr. 9, 1998, "National Cancer Institute, Cancer Genome Anatomy Project," XP002119682.

L. Hillier et al., "The WashU–Merck EST Project," EMBL/Genbank Databases, Accession No. AA147031 Sequence reference HSAA47031, Dec. 14, 1996, XP002119681.

* cited by examiner

Alignment of Frizzled Domains of Human Corin

```
Frizzled      CEPITISICK NIPYNMTIMP NLIGHTKQEE AGL..EVHQF APLVKIGCSD
FZ-1          CQPISIPLCT DIAYNQTIMP NLIGHTNQED AGL..EVHQF YPLVKVQCSA
LIN 17        CIPIDIELCK DLPYNYTYFP NTILHNDQHT LQT..HTEHF KPLMKTKCHP
Corin_Crd1    CMNITHSQCQ MLPYHATLTP LLSVVRNME...MEKFLKFF TYLHRLSCYQ
Corin_Crd2    CEPITLELCM NLPYNSTSYP NYFGHRTQKE ASISWESSLF PALVQTNCYK Frizzled      DLQLFLCSLY VPVCTI.LER P..IPPCRSL CESARV.CEK LMKTYNFNWP
FZ-1          ELKFFLCSMY APVCTV.LEQ A..LPPCRSL CERAQG.CEA LMNKFGFQWP
LIN 17        HIHFFICSVF APMCPIGMPQ A..VTSCKSV CEQVKADCFS ILEEFGIGWP
Corin_Crd1    HIMLFGCTIA FPECIIDGDD SHGLLPCRSF CEAAKEGCES VLGMVNYSWP
Corin_Crd2    YLMFFSCTIL VPKCDVNTGE R..IPPCRAL CEHSKERCES VLGIVGLQWP Frizzled      ENLECSKF~~
FZ-1          DTLKCEKF~~
LIN 17        EPLNCAQFPD
Corin_Crd1    DFLRCSQFRN
Corin_Crd2    EDTDCSQFPE
```

FIGURE 2

Sequence Alignment of the LDLR-Repeats in Corin

```
CORIN LDLR-Repeat 1      ~~CASGICIP  GKLQCNGYND  CDDWNDKAHC
CORIN LDLR-Repeat 2      ~HCPTGNCLN  YSLVCDGYDD  CGDLSDEQNC
CORIN LDLR-Repeat 3      ~RCGDGRCIA  MEWVCDGDHD  CVDKSDEVNC
CORIN LDLR-Repeat 4      ~~CRNGQCIP  STFQCDGDED  CKDGSDEENC
CORIN LDLR-Repeat 5      ~~CRSGQCVL  ASRRCDGQAD  CDDDSDEENC
CORIN LDLR-Repeat 6      ~CPSNKQCLK  HTVICDGFPD  CPDYMDEKNC
CORIN LDLR-Repeat 7      ~ECANHACVS  RDLWCDGEAD  CSDSSDEWDC
Human LDLR consensus     ~~~~G~CI~   ~~~~CD~~~D  C~D~SDE~~~
```

FIGURE 3

Alignment of Human Corin Serine Protease Domain

```
KAL    RIVGGTNSSW  GEWPWQVSLQ  VKLTAQRHLC  GGSLIGHQWV  LTAAHCFDGL
ENTK   KIVGGSNAKE  GAWPWVVGLY  Y...GGRLLC  GASLVSSDWL  VSAAHCVYGR
TRP1   KIVGYNCEE   NSVPYQVSL.  ...NSGXHFC  GGSLINEQWV  VSAGHCYKSR
Corin  RILGGRTSRP  GRWPWQCSLQ  SEPSG..HIC  GCVLIAKWMV  LTVAHCFEGR KAL    PLQ.DVWRIY  SGIILNLSDIT  K.DTPFSQIK  EIIHQNYKV   SEGNEDIALI
ENTK   NLEPSKWTAI  LGLHMKSNLT  SPQTVPRLID  EIVINPHYNR  RRKDNDIAMM
TRP1   ......IQVR  LGEHNIEVLE  GNEQFINAAK  .IIRHPQYDR  KTLNNDIMLI
Corin  E.NAAKWKVV  LGINNL.DHP  SVFMQTRFVK  TIILHPRYSR  AVVDYDISIV KAL    KLQAPLNYTE  FQKPICLPSK  GDTSTIYTNC  WVTGWGFSKE  KG.EIQNILQ
ENTK   HLEFKVNYTD  YIQPICLPEE  NQVFPPGRNC  SIAGWGTVVY  QG.TTANILQ
TRP1   KLSSRAVINA  RVSTISLPTA  PPAT..GTKC  LISGWGNTAS  SGADYPDELQ
Corin  ELSEDISETG  YVRPVCLPNP  EQWLEPDTYC  YITGWGHMGN  KM.PFK..LQ KAL    KVNIPLVTNE  ECQKRYQDYK  ITQRMVCAGY  KEGGKDACKG  DSGGPLVC.K
ENTK   EADVPLLSNE  RCQQQMPEYN  ITENMICAGY  EEGGIDSCQG  DSGGPLMC.Q
TRP1   CLDAPVLSQA  KCEASYPG.K  ITSNMFCVGF  LEGGKDSCQG  DSGGPVVCNG
Corin  EGEVRIISLE  HCQSYFDMKT  ITTRMICAGY  ESGTVDSCMG  DSGGPLVCEK KAL    HNGMWRLVGI  TSWGEGC.AR  REQPGVYTKV  AEYMDWI~~   ~~~~~~~~~~
ENTK   ENNRWFLAGV  TSFGYKC.AL  PNRPGVYARV  SRFTEWIQ~~  I~~~~~~~~~
TRP1   Q.....LQGV  VSWGDGC.AQ  KNKPGVTKV   YNYVKWIKNT  I~~~~~~~~~
Corin  PGGRWTLFGL  TSWGSVCFSK  VLGPGVYSNV  SYFVEWIKRQ  IYIQTFLLN
```

FIGURE 4

SEQUENCE LISTING

<160> NUMBER OF SEQ ID NOS: 34

<210> SEQ ID NO 1
<211> LENGTH: 4933
<212> TYPE: DNA
<213> ORGANISM: Homo sapiens

<400> SEQUENCE: 1

```
aaatcatccg tagtgcctcc ccggggaca cgtagaggag agaaaagcga ccaagataaa      60
agtggacaga agaataagcg agactttta tccatgaaac agtctcctgc cctcgctccg     120
gaagagcgct accgcagagc cgggtccca aagccggtct tgagagctga tgacaataac     180
atgggcaatg gctgctctca gaagctggcg actgctaacc tcctccggtt cctattgctg     240
gtcctgattc catgtatctg tgctctcgtt ctcttgctgg tgatcctgct ttcctatgtt     300
ggaacattac aaaaggtcta ttttaaatca aatgggagtg aacctttggt cactgatggt     360
gaaatccaag ggtccgatgt tattcttaca aatacaattt ataaccagag cactgtggtg     420
tctactgcac atcccgacca acacgttcca gcctggacta cggatgcttc tctcccaggg     480
gaccaaagtc acaggaatac aagtgcctgt atgaacatca cccacagcca gtgtcagatg     540
ctgccctacc acgccacgct gacacctctc ctctcagttg tcagaaacat ggaaatggaa     600
aagttcctca agtttttcac atatctccat cgcctcagtt gctatcaaca tatcatgctg     660
tttggctgta ccctcgcctt ccctgagtgc atcattgatg gcgatgacag tcatggactc     720
ctgccctgta ggtccttctg tgaggctgca aaagaaggct gtgaatcagt cctggggatg     780
gtgaattact cctggccgga tttcctcaga tgctcccagt ttagaaacca aactgaaagc     840
agcaatgtca gcagaatttg cttctcacct cagcaggaaa acgaaagca attgctctgt     900 ggaaggggtg agaactttct gtgtgccagt ggaatctgca tccccgggaa actgcaatgt     960
aatggctaca cgactgtga cgactggagt gacgaggctc attgcaactg cagcgagaat    1020
ctgtttcact gtcacacagg caagtgcctt aattacagcc ttgtgtgtga tggatatgat    1080
gactgtgggg atttgagtga tgagcaaaac tgtgattgca atcccacaac agagcatcgc    1140
tgcggggacg ggcgctgcat cgccatggag tgggtgtgtg atggtgacca cgactgtgtg    1200
gataagtccc acgaggtcaa ctgctcctgt cacagccagg gtctggtgga atgcagaaat    1260
ggacaatgta tccccagcac gtttcaatgt gatggtgacg aggactgcaa ggatgggagt    1320
gatgaggaga actgcagcgt cattcagact tcatgtcaag aaggagacca aagatgcctc    1380
tacaatccct gccttgattc atgtggtggt agctctctct gtgacccgaa caacagtctg    1440
```

-continued

| | |
|---|---|
| aataactgta gtcaatgtga accaattaca ttggaactct gcatgaattt gccctacaac | 1500 |
| agtacaagtt atccaaatta ttttggccac aggactcaaa aggaagcatc catcagctgg | 1560 |
| gagtcttctc ttttccctgc acttgttcaa accaactgtt ataaatacct catgttcttt | 1620 |
| tcttgcacca ttttggtacc aaaatgtgat gtgaatacag gcgagcgtat ccctccttgc | 1680 |
| agggcattgt gtgaacactc taaagaacgc tgtgagtctg ttcttgggat tgtgggccta | 1740 |
| cagtggcctg aagacacaga ttgcagtcaa tttccagagg aaaattcaga caatcaaacc | 1800 |
| tgcctgatgc ctgatgaata tgtggaagaa tgctcaccta gtcatttcaa gtgccgctca | 1860 |
| ggacagtgtg ttctggcttc cagaagatgt gatggccagg ccgactgtga cgatgacagt | 1920 |
| gatgaggaaa actgtggttg taaagagaga gatctttggg aatgtccatc caataaacaa | 1980 |
| tgtttgaagc acacagtgat ctgcgatggg ttcccagact gccctgatta catggacgag | 2040 |
| aaaaactgct cattttgcca agatgatgag ctggaatgtg caaaccatgc gtgtgtgtca | 2100 |
| cgtgacctgt ggtgtgatgg tgaagccgac tgctcagaca gttcagatga atgggactgt | 2160 |
| gtgaccctct ctataaatgt gaactcctct tcctttctga tggttcacag agctgccaca | 2220 |
| gaacaccatg tgtgtgcaga tggctggcag gagatattga gtcagctggc ctgcaagcag | 2280 |
| atgggtttag gagaaccatc tgtgaccaaa ttgatacagg aacaggagaa agagccgcgg | 2340 |
| tggctgacat tacactccaa ctgggagagc tcaatgggga ccactttaca tgaacttcta | 2400 |
| gtaaatgggc agtcttgtga gcagaagt aaaatttctc ttctgtgtac taaacaagac | 2460 |
| tgtgggcgcc gccctgctgc ccgaatgaac aaaaggatcc ttggaggtcg acgagtcgc | 2520 |
| cctggaaggt ggccatggca gtgttctctg cagagtgaac ccagtggaca tatctgtggc | 2580 |
| tgtgtcctca ttgccaagaa gtgggttctg acagttgccc actgcttcga ggggagagag | 2640 |
| aatgctgcag tttggaaagt ggtgcttggc atcaacaatc tagaccatcc atcagtgttc | 2700 |
| atgcagacac gctttgtgaa gaccatcatc ctgcatcccc gctacagtcg agcagtggtg | 2760 |
| gactatgaca tcagcatcgt tgagctgagt gaagacatca gtgagactgg ctacgtccgg | 2820 |
| cctgtctgct tgcccaaccc ggagcagtgg ctagagcctg acacgtactg ctatatcaca | 2880 |
| ggctggggcc acatgggcaa taaaatgcca tttaagctgc aagagggaga ggtccgcatt | 2940 |
| atttctctgg aacattgtca gtcctacttt gacatgaaga ccatcaccac tcggatgata | 3000 |
| tgtgctggct atgagtctgg cacagttgat tcatgcatgg gtgacagcgg tgggcctctt | 3060 |
| gtttgtgaga agcctggagg acggtggaca ttatttggat taacttcatg gggctccgtc | 3120 |
| tgcttttcca aagtcctggg gcctggcgtt tatagtaatg tgtcatattt cgtcgaatgg | 3180 |
| attaaaagac agatttacat ccagaccttt ctcctaaact aattataagg atgatcagag | 3240 |
| acttttgcca gctacactaa aagaaaatgg ccttcttgac tgtgaagagc tgcctgcaga | 3300 |
| gagctgtaca gaagcacttt tcatggacag aaatgctcaa tcgtgcactg caaatttgca | 3360 |
| tgtttgtttt ggactaattt ttttcaattt attttttcac cttcattttt ctcttatttc | 3420 |
| aagttcaatg aaagacttta caaaagcaaa caaagcagac tttgtccttt tgccaggcct | 3480 |
| aaccatgact gcagcacaaa attatcgact ctggcgagat ttaaaatcag gtgctacagt | 3540 |
| aacaggttat ggaatggtct cttttatcct atcacaaaaa aagacataga tatttaggct | 3600 |
| gattaattat ctctaccagt ttttgtttct caagctcagt gcatagtggt aaatttcagt | 3660 |
| gttaacattg gagacttgct tttcttttc ttttttttata ccccacaatt cttttttatt | 3720 |
| acacttcgaa tttagggta cacgagcaca acgtgcaggt tagttacata tgtatacatg | 3780 |
| tgccatgttg gtgtgctgaa cccagtaact cgtcatttga tttattaaaa gccaagataa | 3840 |

-continued

```
tttacatgtt taaagtattt actattaccc ccttctaatg tttgcataat tctgagaact    3900
gataaaagac agcaataaaa gaccagtgtc atccatttag gtagcaagac atattgaatg    3960
caaagttctt tagatatcaa tattaacact tgacattatt ggaccccca ttctggatgt    4020 atatcaagat cataatttta tagaagagtc tctatagaac tgtcctcata gctgggtttg    4080
ttcaggatat atgagttggc tgattgagac tgcaacaact acatctatat ttatgggcaa    4140
tattttgttt tacttatgtg gcaaagaact ggatattaaa ctttgcaaaa gagaatttag    4200
atgagagatg caatttttta aaagaaaat taatttgcat ccctcgttta attaaattta    4260
tttttcagtt ttcttgcgtt catccatacc aacaaagtca taaagagcat attttagagc    4320
acagtaagac tttgcatgga gtaaaacatt ttgtaatttt cctcaaaaga tgtttaatat    4380
ctggtttctt ctcattggta attaaaattt tagaaatgat ttttagctct aggccacttt    4440
acgcaactca atttctgaag caattagtgg taaaaagtat ttttccccac taaaaaactt    4500
taaaacacaa atcttcatat atacttaatt taattagtca ggcatccatt ttgccttta    4560 aacaactagg attccctact aacctccacc agcaacctgg actgcctcag cattccaaat    4620
agatactacc tgcaatttta tacatgtatt tttgtatctt ttctgtgtgt aaacatagtt    4680
gaaattcaaa aagttgtagc aatttctata ctattcatct cctgtccttc agtttgtata    4740
aacctaagga gagtgtgaaa tccagcaact gaattgtggt cacgattgta tgaaagttca    4800
agaacatatg tcagttttgt tacagttgta gctacatact caatgtatca actttttagcc   4860 tgctcaactt aggctcagtg aaatatatat attatactta ttttaaataa ttcttaatac    4920
aaataaaatg gta                                                      4933
```

<210> SEQ ID NO 2
<211> LENGTH: 1042
<212> TYPE: PRT
<213> ORGANISM: Homo sapiens

<400> SEQUENCE: 2

```
Met Lys Gln Ser Pro Ala Leu Ala Pro Glu Glu Arg Tyr Arg Arg Ala
 1               5                  10                  15

Gly Ser Pro Lys Pro Val Leu Arg Ala Asp Asp Asn Asn Met Gly Asn
             20                  25                  30

Gly Cys Ser Gln Lys Leu Ala Thr Ala Asn Leu Leu Arg Phe Leu Leu
         35                  40                  45

Leu Val Leu Ile Pro Cys Ile Cys Ala Leu Val Leu Leu Val Ile
     50                  55                  60

Leu Leu Ser Tyr Val Gly Thr Leu Gln Lys Val Tyr Phe Lys Ser Asn
 65                  70                  75                  80

Gly Ser Glu Pro Leu Val Thr Asp Gly Glu Ile Gln Gly Ser Asp Val
                 85                  90                  95

Ile Leu Thr Asn Thr Ile Tyr Asn Gln Ser Thr Val Val Ser Thr Ala
            100                 105                 110

His Pro Asp Gln His Val Pro Ala Trp Thr Thr Asp Ala Ser Leu Pro
        115                 120                 125

Gly Asp Gln Ser His Arg Asn Thr Ser Ala Cys Met Asn Ile Thr His
    130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
                165                 170                 175
```

```
Tyr Leu His Arg Leu Ser Cys Tyr Gln His Ile Met Leu Phe Gly Cys
            180                 185                 190

Thr Leu Ala Phe Pro Glu Cys Ile Ile Asp Gly Asp Ser His Gly
            195                 200                 205

Leu Leu Pro Cys Arg Ser Phe Cys Glu Ala Ala Lys Glu Gly Cys Glu
            210                 215                 220

Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
            260                 265                 270

Glu Asn Phe Leu Cys Ala Ser Gly Ile Cys Ile Pro Gly Lys Leu Gln
            275                 280                 285

Cys Asn Gly Tyr Asn Asp Cys Asp Asp Trp Ser Asp Glu Ala His Cys
            290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
            340                 345                 350

Gly Arg Cys Ile Ala Met Glu Trp Val Cys Asp Gly Asp His Asp Cys
            355                 360                 365

Val Asp Lys Ser Asp Glu Val Asn Cys Ser Cys His Ser Gln Gly Leu
            370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Glu Asn Cys Ser Val
                405                 410                 415

Ile Gln Thr Ser Cys Gln Glu Gly Asp Gln Arg Cys Leu Tyr Asn Pro
            420                 425                 430

Cys Leu Asp Ser Cys Gly Gly Ser Ser Leu Cys Asp Pro Asn Asn Ser
            435                 440                 445

Leu Asn Asn Cys Ser Gln Cys Glu Pro Ile Thr Leu Glu Leu Cys Met
            450                 455                 460

Asn Leu Pro Tyr Asn Ser Thr Ser Tyr Pro Asn Tyr Phe Gly His Arg
465                 470                 475                 480

Thr Gln Lys Glu Ala Ser Ile Ser Trp Glu Ser Ser Leu Phe Pro Ala
                485                 490                 495

Leu Val Gln Thr Asn Cys Tyr Lys Tyr Leu Met Phe Phe Ser Cys Thr
            500                 505                 510

Ile Leu Val Pro Lys Cys Asp Val Asn Thr Gly Glu Arg Ile Pro Pro
            515                 520                 525

Cys Arg Ala Leu Cys Glu His Ser Lys Glu Arg Cys Glu Ser Val Leu
530                 535                 540

Gly Ile Val Gly Leu Gln Trp Pro Glu Asp Thr Asp Cys Ser Gln Phe
545                 550                 555                 560

Pro Glu Glu Asn Ser Asp Asn Gln Thr Cys Leu Met Pro Asp Glu Tyr
                565                 570                 575

Val Glu Glu Cys Ser Pro Ser His Phe Lys Cys Arg Ser Gly Gln Cys
            580                 585                 590
```

-continued

```
Val Leu Ala Ser Arg Arg Cys Asp Gly Gln Ala Asp Cys Asp Asp
            595                 600                 605

Ser Asp Glu Glu Asn Cys Gly Cys Lys Glu Arg Asp Leu Trp Glu Cys
    610                 615                 620

Pro Ser Asn Lys Gln Cys Leu Lys His Thr Val Ile Cys Asp Gly Phe
625                 630                 635                 640

Pro Asp Cys Pro Asp Tyr Met Asp Glu Lys Asn Cys Ser Phe Cys Gln
                645                 650                 655

Asp Asp Glu Leu Glu Cys Ala Asn His Ala Cys Val Ser Arg Asp Leu
            660                 665                 670

Trp Cys Asp Gly Glu Ala Asp Cys Ser Asp Ser Ser Asp Glu Trp Asp
        675                 680                 685

Cys Val Thr Leu Ser Ile Asn Val Asn Ser Ser Ser Phe Leu Met Val
    690                 695                 700

His Arg Ala Ala Thr Glu His His Val Cys Ala Asp Gly Trp Gln Glu
705                 710                 715                 720

Ile Leu Ser Gln Leu Ala Cys Lys Gln Met Gly Leu Gly Glu Pro Ser
                725                 730                 735

Val Thr Lys Leu Ile Gln Glu Gln Glu Lys Glu Pro Arg Trp Leu Thr
            740                 745                 750

Leu His Ser Asn Trp Glu Ser Leu Asn Gly Thr Thr Leu His Glu Leu
        755                 760                 765

Leu Val Asn Gly Gln Ser Cys Glu Ser Arg Ser Lys Ile Ser Leu Leu
    770                 775                 780

Cys Thr Lys Gln Asp Cys Gly Arg Arg Pro Ala Ala Arg Met Asn Lys
785                 790                 795                 800

Arg Ile Leu Gly Gly Arg Thr Ser Arg Pro Gly Arg Trp Pro Trp Gln
                805                 810                 815

Cys Ser Leu Gln Ser Glu Pro Ser Gly His Ile Cys Gly Cys Val Leu
            820                 825                 830

Ile Ala Lys Lys Trp Val Leu Thr Val Ala His Cys Phe Glu Gly Arg
        835                 840                 845

Glu Asn Ala Ala Val Trp Lys Val Val Leu Gly Ile Asn Asn Leu Asp
    850                 855                 860

His Pro Ser Val Phe Met Gln Thr Arg Phe Val Lys Thr Ile Ile Leu
865                 870                 875                 880

His Pro Arg Tyr Ser Arg Ala Val Val Asp Tyr Asp Ile Ser Ile Val
                885                 890                 895

Glu Leu Ser Glu Asp Ile Ser Glu Thr Gly Tyr Val Arg Pro Val Cys
            900                 905                 910

Leu Pro Asn Pro Glu Gln Trp Leu Glu Pro Asp Thr Tyr Cys Tyr Ile
        915                 920                 925

Thr Gly Trp Gly His Met Gly Asn Lys Met Pro Phe Lys Leu Gln Glu
    930                 935                 940

Gly Glu Val Arg Ile Ile Ser Leu Glu His Cys Gln Ser Tyr Phe Asp
945                 950                 955                 960

Met Lys Thr Ile Thr Thr Arg Met Ile Cys Ala Gly Tyr Glu Ser Gly
                965                 970                 975

Thr Val Asp Ser Cys Met Gly Asp Ser Gly Gly Pro Leu Val Cys Glu
            980                 985                 990

Lys Pro Gly Gly Arg Trp Thr Leu Phe Gly Leu Thr Ser Trp Gly Ser
        995                 1000                1005

Val Cys Phe Ser Lys Val Leu Gly Pro Gly Val Tyr Ser Asn Val Ser
```

```
                1010                1015                1020
Tyr Phe Val Glu Trp Ile Lys Arg Gln Ile Tyr Ile Gln Thr Phe Leu
1025                1030                1035                1040

Leu Asn

<210> SEQ ID NO 3
<211> LENGTH: 3547
<212> TYPE: DNA
<213> ORGANISM: Mus sp.

<400> SEQUENCE: 3
gtggcagacg gtccctcact cctgtggctt ggcgtcggag acgctggcag tcatgggcag       60
ggtttccttc agcgttcggg tcagctccgt gcggagagcc cgctgctctt gtcctgggcg      120
atgctacctc tcctgcagag tccctccaac caccgccctc cgtgcactga acggtcttgg      180
ctgcgcgggg gttccggggg agactgcagg tggagccgtc ggacccggcc ccttggggac      240
ccgtggcttc ctctccgggt ccaagttcca ggctcccggc agctggaagg attgctttgg      300
agccccgcct gctccagacg tcttgagagc agacaggagc gtgggcgagg gctgtcctca      360
gaagctggtg actgctaact tgctgcgctt cctcctgctg gtgctcatcc cctgcatctg      420
cgccctcatc gtgctgctgg ccatcctgct gtcctttgtg gaacattaa aaagggttta      480
tttcaaatca aatgacagtg aacctttggt cactgatggg gaagctcgag tgcctggtgt      540
tattcctgta aatacagttt attatgagaa cacaggggcg ccctctctgc ccccagcca      600
gtccactcca gcctggacac cgagagctcc ttctccagag gaccagagtc acaggaacac      660
aagcacctgc atgaacatca ctcacagcca gtgtcaaatt ctgccctacc acagcacgtt      720
ggcacctctc ttgccaattg tcaaaaacat ggacatggaa aagttcctca gttcttcac      780
gtacctccat cgcctcagtt gctatcaaca tatcctgctc ttcggctgta gcctcgcctt      840
ccctgagtgc gttgttgatg gcgatgacag gcaaggtctt ctaccctgta gatctttctg      900
tgaggctgct aaagaaggat gcgaatctgt cctgggaatg gtgaactcct cctggccgga      960
ttccctcaga tgctctcagt ttagggacca cactgagact aacagcagtg tcagaaagag     1020
ctgcttctca ctgcagcagg aacatggaaa gcaatcactc tgtggagggg gcgagagctt     1080
cctgtgtacc agcgggctct cgtccccaa gaagctgcag tgtaacggct ataatgactg     1140
tgatgactgg agcgacgagg cgcattgcaa ctgcagcaag gatctgtttc actgtggcac     1200
aggcaagtgc ctccattaca gcctcttgtg tgatgggtac gatgactgtg gggacctgag     1260
tgacgagcaa aactgtgatt gtaatctcac aaaagagcat cgctgtggag atgggcgctg     1320
cattgcggct gagtgggtgt gcgatgggga ccatgactgt gtggacaagt ctgatgaggt     1380
caactgctct tgtcacagcc agggcctggt ggaatgcaga agtggacagt gcatccctag     1440
caccttccag tgtgatgggg acgaagactg taaggatggg agtgacgagg agaactgcag     1500
tgacagtcag acgccatgtc agaaggaga acagggatgc cttggcagtt cctgcgtcga     1560
atcctgtgct ggtagctctc tgtgtgactc agacagcagc tgagtaact gcagtcaatg     1620
tgagcccatc actttggaac tctgcatgaa tttgccctac aaccatacac attatccaaa     1680
ttaccttggc cacagaactc aaaaggaagc gtccatcagc tgggagtcat cccttttccc     1740
tgcccttgta caaaccaact gttacaaata cctcatgttt ttcgcttgca ccattttggt     1800
tccaaagtgt gatgtgaata caggacaacg catcccgcct tgcagactcc tgtgtgagca     1860
ctccaaagag cgctgtgagt ctgttctggg aatcgttggc ctgcagtggc ctgaagacac     1920
```

-continued

```
cgactgcaat caatttccag aggaaagttc agacaatcaa acttgcctcc tgcccaatga    1980
agatgtggaa gaatgctctc cgagtcactt caaatgccgc tcgggacgat gcgttctggg    2040
ctccaggaga tgtgacggcc aggctgactg tgacgacgac agtgacgagg agaactgtgg    2100
ttgtaaagag agagctcttt gggaatgtcc atttaataag caatgtctga agcatacatt    2160
aatctgcgat gggtttccag attgtccaga cagtatggat gaaaaaaact gctcattttg    2220
ccaagacaat gagctggaat gtgccaacca tgagtgtgtg ccgcgtgacc tttggtgcga    2280
cggatgggtc gactgctcag acagttctga tgaatgggc tgtgtgaccc tctctaaaaa    2340
tgggaactct tcctcattgc tgactgttca caaatctgca aggaacacc acgtgtgtgc    2400 tgacggctgg cgggagacgt tgagtcagct ggcctgcaag cagatgggtt taggagaacc    2460
gtctgtgacc aagctgatcc caggacagga aggccagcag tggctgaggt tgtaccccaa    2520
ctgggagaat ctcaatggga gcaccttgca ggagctgctg gtatacaggc actcctgccc    2580
aagcagaagt gagatttccc ttctgtgctc caagcaagac tgtggccgcc gccctgctgc    2640
ccgaatgaac aagaggatcc ttggggtcg gactagtcgt cctgggaggt ggccgtggca    2700
gtgctctctg cagagtgaac ccagtggaca tatctgtggc tgtgtcctca ttgccaagaa    2760
gtgggtcctg acagttgccc attgctttga agggagagaa gacgctgatg tttggaaagt    2820
ggtatttggc ataaacaacc tggaccatcc atcaggcttc atgcagaccc gctttgtgaa    2880
gaccatcctg ctacatcccc gttacagtcg agcagtggta gactatgata tcagcgtggt    2940
ggagctgagc gatgatatca atgagacaag ctacgtcaga cctgtctgcc tacccagtcc    3000
ggaggagtat ctagaaccag atacgtactg ctacatcaca ggctggggcc acatgggcaa    3060
taaaatgccc tttaagctgc aggagggaga ggtccgcatt atccctctgg agcagtgcca    3120
gtcctatttt gacatgaaga ccatcaccaa tcggatgatc tgtgctggct atgagtctgg    3180
caccgtggac tcctgcatgg gagacagcgg tgggcctctg gtttgtgaac gacccggagg    3240
acagtggaca ttatttggtt taacttcatg gggctccgtc tgcttttcca aagttctggg    3300
acctggagtg tacagcaatg tgtcttactt tgtgggctgg attgaaagac aaatatatat    3360
ccagaccttt ctccaaaaga aatcccaagg ataatcagag actttgtggg gaaacctaca    3420
tggagaatga ccctctgaaa cagaagcttg tcctgccaag agctgtacga acaggcgttt    3480
cacggacagg acgctcaaca tgcaccgcaa gatctctcct gtttgtgcta gatgagtttt    3540
actcagg                                                             3547
```

<210> SEQ ID NO 4
<211> LENGTH: 1113
<212> TYPE: PRT
<213> ORGANISM: Mus sp.

<400> SEQUENCE: 4

```
Met Gly Arg Val Ser Phe Ser Val Arg Val Ser Val Arg Arg Ala
  1               5                  10                  15

Arg Cys Ser Cys Pro Gly Arg Cys Tyr Leu Ser Cys Arg Val Pro Pro
                 20                  25                  30

Thr Thr Ala Leu Arg Ala Leu Asn Gly Leu Gly Cys Ala Gly Val Pro
             35                  40                  45

Gly Glu Thr Ala Gly Gly Ala Val Gly Pro Gly Pro Leu Gly Thr Arg
         50                  55                  60

Gly Phe Leu Ser Gly Ser Lys Phe Gln Ala Pro Gly Ser Trp Lys Asp
 65                  70                  75                  80
```

-continued

```
Cys Phe Gly Ala Pro Ala Pro Asp Val Leu Arg Ala Asp Arg Ser
            85              90              95

Val Gly Glu Gly Cys Pro Gln Lys Leu Val Thr Ala Asn Leu Leu Arg
            100             105             110

Phe Leu Leu Leu Val Leu Ile Pro Cys Ile Cys Ala Leu Ile Val Leu
            115             120             125

Leu Ala Ile Leu Leu Ser Phe Val Gly Thr Leu Lys Arg Val Tyr Phe
130             135             140

Lys Ser Asn Asp Ser Glu Pro Leu Val Thr Asp Gly Glu Ala Arg Val
145             150             155             160

Pro Gly Val Ile Pro Val Asn Thr Val Tyr Glu Asn Thr Gly Ala
            165             170             175

Pro Ser Leu Pro Pro Ser Gln Ser Thr Pro Ala Trp Thr Pro Arg Ala
            180             185             190

Pro Ser Pro Glu Asp Gln Ser His Arg Asn Thr Ser Thr Cys Met Asn
            195             200             205

Ile Thr His Ser Gln Cys Gln Ile Leu Pro Tyr His Ser Thr Leu Ala
    210             215             220

Pro Leu Leu Pro Ile Val Lys Asn Met Asp Met Glu Lys Phe Leu Lys
225             230             235             240

Phe Phe Thr Tyr Leu His Arg Leu Ser Cys Tyr Gln His Ile Leu Leu
            245             250             255

Phe Gly Cys Ser Leu Ala Phe Pro Glu Cys Val Val Asp Gly Asp Asp
            260             265             270

Arg Gln Gly Leu Leu Pro Cys Arg Ser Phe Cys Glu Ala Ala Lys Glu
            275             280             285

Gly Cys Glu Ser Val Leu Gly Met Val Asn Ser Ser Trp Pro Asp Ser
    290             295             300

Leu Arg Cys Ser Gln Phe Arg Asp His Thr Glu Thr Asn Ser Ser Val
305             310             315             320

Arg Lys Ser Cys Phe Ser Leu Gln Gln Glu His Gly Lys Gln Ser Leu
            325             330             335

Cys Gly Gly Gly Glu Ser Phe Leu Cys Thr Ser Gly Leu Cys Val Pro
            340             345             350

Lys Lys Leu Gln Cys Asn Gly Tyr Asn Asp Cys Asp Asp Trp Ser Asp
            355             360             365

Glu Ala His Cys Asn Cys Ser Lys Asp Leu Phe His Cys Gly Thr Gly
    370             375             380

Lys Cys Leu His Tyr Ser Leu Leu Cys Asp Gly Tyr Asp Asp Cys Gly
385             390             395             400

Asp Leu Ser Asp Glu Gln Asn Cys Asp Cys Asn Leu Thr Lys Glu His
            405             410             415

Arg Cys Gly Asp Gly Arg Cys Ile Ala Ala Glu Trp Val Cys Asp Gly
            420             425             430

Asp His Asp Cys Val Asp Lys Ser Asp Glu Val Asn Cys Ser Cys His
    435             440             445

Ser Gln Gly Leu Val Glu Cys Arg Ser Gly Gln Cys Ile Pro Ser Thr
            450             455             460

Phe Gln Cys Asp Gly Asp Glu Asp Cys Lys Asp Gly Ser Asp Glu Glu
465             470             475             480

Asn Cys Ser Asp Ser Gln Thr Pro Cys Pro Glu Gly Glu Gln Gly Cys
            485             490             495

Leu Gly Ser Ser Cys Val Glu Ser Cys Ala Gly Ser Ser Leu Cys Asp
```

-continued

```
                500             505             510
Ser Asp Ser Ser Leu Ser Asn Cys Ser Gln Cys Glu Pro Ile Thr Leu
        515             520             525
Glu Leu Cys Met Asn Leu Pro Tyr Asn His Thr His Tyr Pro Asn Tyr
        530             535             540
Leu Gly His Arg Thr Gln Lys Glu Ala Ser Ile Ser Trp Glu Ser Ser
545             550             555             560
Leu Phe Pro Ala Leu Val Gln Thr Asn Cys Tyr Lys Tyr Leu Met Phe
                565             570             575
Phe Ala Cys Thr Ile Leu Val Pro Lys Cys Asp Val Asn Thr Gly Gln
                580             585             590
Arg Ile Pro Pro Cys Arg Leu Leu Cys Glu His Ser Lys Glu Arg Cys
                595             600             605
Glu Ser Val Leu Gly Ile Val Gly Leu Gln Trp Pro Glu Asp Thr Asp
        610             615             620
Cys Asn Gln Phe Pro Glu Glu Ser Ser Asp Asn Gln Thr Cys Leu Leu
625             630             635             640
Pro Asn Glu Asp Val Glu Glu Cys Ser Pro Ser His Phe Lys Cys Arg
                645             650             655
Ser Gly Arg Cys Val Leu Gly Ser Arg Arg Cys Asp Gly Gln Ala Asp
                660             665             670
Cys Asp Asp Asp Ser Asp Glu Glu Asn Cys Gly Cys Lys Glu Arg Ala
        675             680             685
Leu Trp Glu Cys Pro Phe Asn Lys Gln Cys Leu Lys His Thr Leu Ile
        690             695             700
Cys Asp Gly Phe Pro Asp Cys Pro Asp Ser Met Asp Glu Lys Asn Cys
705             710             715             720
Ser Phe Cys Gln Asp Asn Glu Leu Glu Cys Ala Asn His Glu Cys Val
                725             730             735
Pro Arg Asp Leu Trp Cys Asp Gly Trp Val Asp Cys Ser Asp Ser Ser
                740             745             750
Asp Glu Trp Gly Cys Val Thr Leu Ser Lys Asn Gly Asn Ser Ser Ser
        755             760             765
Leu Leu Thr Val His Lys Ser Ala Lys Glu His His Val Cys Ala Asp
        770             775             780
Gly Trp Arg Glu Thr Leu Ser Gln Leu Ala Cys Lys Gln Met Gly Leu
785             790             795             800
Gly Glu Pro Ser Val Thr Lys Leu Ile Pro Gly Gln Glu Gly Gln Gln
                805             810             815
Trp Leu Arg Leu Tyr Pro Asn Trp Glu Asn Leu Asn Gly Ser Thr Leu
                820             825             830
Gln Glu Leu Leu Val Tyr Arg His Ser Cys Pro Ser Arg Ser Glu Ile
        835             840             845
Ser Leu Leu Cys Ser Lys Gln Asp Cys Gly Arg Arg Pro Ala Ala Arg
        850             855             860
Met Asn Lys Arg Ile Leu Gly Gly Arg Thr Ser Arg Pro Gly Arg Trp
865             870             875             880
Pro Trp Gln Cys Ser Leu Gln Ser Glu Pro Ser Gly His Ile Cys Gly
                885             890             895
Cys Val Leu Ile Ala Lys Lys Trp Val Leu Thr Val Ala His Cys Phe
                900             905             910
Glu Gly Arg Glu Asp Ala Asp Val Trp Lys Val Val Phe Gly Ile Asn
        915             920             925
```

```
Asn Leu Asp His Pro Ser Gly Phe Met Gln Thr Arg Phe Val Lys Thr
    930                 935                 940

Ile Leu Leu His Pro Arg Tyr Ser Arg Ala Val Val Asp Tyr Asp Ile
945                 950                 955                 960

Ser Val Val Glu Leu Ser Asp Asp Ile Asn Glu Thr Ser Tyr Val Arg
                965                 970                 975

Pro Val Cys Leu Pro Ser Pro Glu Glu Tyr Leu Glu Pro Asp Thr Tyr
            980                 985                 990

Cys Tyr Ile Thr Gly Trp Gly His Met Gly Asn Lys Met Pro Phe Lys
        995                 1000                1005

Leu Gln Glu Gly Glu Val Arg Ile Ile Pro Leu Glu Gln Cys Gln Ser
    1010                1015                1020

Tyr Phe Asp Met Lys Thr Ile Thr Asn Arg Met Ile Cys Ala Gly Tyr
1025                1030                1035                1040

Glu Ser Gly Thr Val Asp Ser Cys Met Gly Asp Ser Gly Gly Pro Leu
                1045                1050                1055

Val Cys Glu Arg Pro Gly Gly Gln Trp Thr Leu Phe Gly Leu Thr Ser
            1060                1065                1070

Trp Gly Ser Val Cys Phe Ser Lys Val Leu Gly Pro Gly Val Tyr Ser
        1075                1080                1085

Asn Val Ser Tyr Phe Val Gly Trp Ile Glu Arg Gln Ile Tyr Ile Gln
    1090                1095                1100

Thr Phe Leu Gln Lys Lys Ser Gln Gly
1105                1110

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
cagttggttt gaacaagtgc aggg                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
tgcaaggagg gatacgctcg cctg                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
aatcccaaga acagactcac agcg                                          24

<210> SEQ ID NO 8
<211> LENGTH: 24
<212> TYPE: DNA
<213> ORGANISM: Artificial Sequence
<220> FEATURE:
```

```
<223> OTHER INFORMATION: Description of Artificial Sequence: Primer

<400> SEQUENCE: 8
cgggtcacag agagagctac cacc                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
ggtctccttc ttgacatgaa tctg                                              24

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
aacaaaacga tccttggagg tcggacgagt                                        30

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
tcttctgtgt actaaacaag actg                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 12
aggccccagg actttggaaa agca                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
acagtggcct gaagacacag attg                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
acagagcatc gctgcgggga cggg                                              24
```

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
aacaaaagga tccttggagg tcggacgagt                                          30

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 16
cggagcccca tgaagttaat cca                                                 23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
gtcaatgtcc caaacgtcac caga                                                24

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
atttcgggaa tgctgagaaa acagacaga                                           29

<210> SEQ ID NO 19
<211> LENGTH: 102
<212> TYPE: PRT
<213> ORGANISM: Homo sapiens

<400> SEQUENCE: 19

Cys Glu Pro Ile Thr Ile Ser Ile Cys Lys Asn Ile Pro Tyr Asn Met
  1               5                  10                  15

Thr Ile Met Pro Asn Leu Ile Gly His Thr Lys Gln Glu Glu Ala Gly
             20                  25                  30

Leu Glu Val His Gln Phe Ala Pro Leu Val Lys Ile Gly Cys Ser Asp
         35                  40                  45

Asp Leu Gln Leu Phe Leu Cys Ser Leu Tyr Val Pro Val Cys Thr Ile
     50                  55                  60

Leu Glu Arg Pro Ile Pro Pro Cys Arg Ser Leu Cys Glu Ser Ala Arg
 65                  70                  75                  80

Val Cys Glu Lys Leu Met Lys Thr Tyr Asn Phe Asn Trp Pro Glu Asn
                 85                  90                  95

Leu Glu Cys Ser Lys Phe
            100

<210> SEQ ID NO 20
<211> LENGTH: 102
```

```
<212> TYPE: PRT
<213> ORGANISM: Homo sapiens

<400> SEQUENCE: 20

Cys Gln Pro Ile Ser Ile Pro Leu Cys Thr Asp Ile Ala Tyr Asn Gln
 1               5                  10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
    50                  55                  60

Leu Glu Gln Ala Leu Pro Pro Cys Arg Ser Leu Cys Glu Arg Ala Gln
65                  70                  75                  80

Gly Cys Glu Ala Leu Met Asn Lys Phe Gly Phe Gln Trp Pro Asp Thr
                85                  90                  95

Leu Lys Cys Glu Lys Phe
            100

<210> SEQ ID NO 21
<211> LENGTH: 106
<212> TYPE: PRT
<213> ORGANISM: Homo sapiens

<400> SEQUENCE: 21

Cys Ile Pro Ile Asp Ile Glu Leu Cys Lys Asp Leu Pro Tyr Asn Tyr
 1               5                  10                  15

Thr Tyr Phe Pro Asn Thr Ile Leu His Asn Asp Gln His Thr Leu Gln
            20                  25                  30

Thr His Thr Glu His Phe Lys Pro Leu Met Lys Thr Lys Cys His Pro
        35                  40                  45

His Ile His Phe Phe Ile Cys Ser Val Phe Ala Pro Met Cys Pro Ile
    50                  55                  60

Gly Met Pro Gln Ala Val Thr Ser Cys Lys Ser Val Cys Glu Gln Val
65                  70                  75                  80

Lys Ala Asp Cys Phe Ser Ile Leu Glu Glu Phe Gly Ile Gly Trp Pro
                85                  90                  95

Glu Pro Leu Asn Cys Ala Gln Phe Pro Asp
            100                 105

<210> SEQ ID NO 22
<211> LENGTH: 107
<212> TYPE: PRT
<213> ORGANISM: Homo sapiens

<400> SEQUENCE: 22

Cys Met Asn Ile Thr His Ser Gln Cys Gln Met Leu Pro Tyr His Ala
 1               5                  10                  15

Thr Leu Thr Pro Leu Leu Ser Val Val Arg Asn Met Glu Met Glu Lys
            20                  25                  30

Phe Leu Lys Phe Phe Thr Tyr Leu His Arg Leu Ser Cys Tyr Gln His
        35                  40                  45

Ile Met Leu Phe Gly Cys Thr Leu Ala Phe Pro Glu Cys Ile Ile Asp
    50                  55                  60

Gly Asp Asp Ser His Gly Leu Leu Pro Cys Arg Ser Phe Cys Glu Ala
65                  70                  75                  80

Ala Lys Glu Gly Cys Glu Ser Val Leu Gly Met Val Asn Tyr Ser Trp
```

```
                          85                  90                  95
Pro Asp Phe Leu Arg Cys Ser Gln Phe Arg Asn
                    100                 105

<210> SEQ ID NO 23
<211> LENGTH: 108
<212> TYPE: PRT
<213> ORGANISM: Homo sapiens

<400> SEQUENCE: 23

Cys Glu Pro Ile Thr Leu Glu Leu Cys Met Asn Leu Pro Tyr Asn Ser
  1               5                  10                  15

Thr Ser Tyr Pro Asn Tyr Phe Gly His Arg Thr Gln Lys Glu Ala Ser
             20                  25                  30

Ile Ser Trp Glu Ser Ser Leu Phe Pro Ala Leu Val Gln Thr Asn Cys
         35                  40                  45

Tyr Lys Tyr Leu Met Phe Phe Ser Cys Thr Ile Leu Val Pro Lys Cys
     50                  55                  60

Asp Val Asn Thr Gly Glu Arg Ile Pro Pro Cys Arg Ala Leu Cys Glu
 65                  70                  75                  80

His Ser Lys Glu Arg Cys Glu Ser Val Leu Gly Ile Val Gly Leu Gln
                 85                  90                  95

Trp Pro Glu Asp Thr Asp Cys Ser Gln Phe Pro Glu
            100                 105

<210> SEQ ID NO 24
<211> LENGTH: 28
<212> TYPE: PRT
<213> ORGANISM: Homo sapiens

<400> SEQUENCE: 24

Cys Ala Ser Gly Ile Cys Ile Pro Gly Lys Leu Gln Cys Asn Gly Tyr
  1               5                  10                  15

Asn Asp Cys Asp Asp Trp Asn Asp Lys Ala His Cys
             20                  25

<210> SEQ ID NO 25
<211> LENGTH: 29
<212> TYPE: PRT
<213> ORGANISM: Homo sapiens

<400> SEQUENCE: 25

His Cys Pro Thr Gly Asn Cys Leu Asn Tyr Ser Leu Val Cys Asp Gly
  1               5                  10                  15

Tyr Asp Asp Cys Gly Asp Leu Ser Asp Glu Gln Asn Cys
             20                  25

<210> SEQ ID NO 26
<211> LENGTH: 29
<212> TYPE: PRT
<213> ORGANISM: Homo sapiens

<400> SEQUENCE: 26

Arg Cys Gly Asp Gly Arg Cys Ile Ala Met Glu Trp Val Cys Asp Gly
  1               5                  10                  15

Asp His Asp Cys Val Asp Lys Ser Asp Glu Val Asn Cys
             20                  25

<210> SEQ ID NO 27
<211> LENGTH: 28
```

-continued

```
<212> TYPE: PRT
<213> ORGANISM: Homo sapiens

<400> SEQUENCE: 27

Cys Arg Asn Gly Gln Cys Ile Pro Ser Thr Phe Gln Cys Asp Gly Asp
  1               5                  10                  15

Glu Asp Cys Lys Asp Gly Ser Asp Glu Glu Asn Cys
             20                  25

<210> SEQ ID NO 28
<211> LENGTH: 28
<212> TYPE: PRT
<213> ORGANISM: Homo sapiens

<400> SEQUENCE: 28

Cys Arg Ser Gly Gln Cys Val Leu Ala Ser Arg Arg Cys Asp Gly Gln
  1               5                  10                  15

Ala Asp Cys Asp Asp Asp Ser Asp Glu Glu Asn Cys
             20                  25

<210> SEQ ID NO 29
<211> LENGTH: 29
<212> TYPE: PRT
<213> ORGANISM: Homo sapiens

<400> SEQUENCE: 29

Cys Pro Ser Asn Lys Gln Cys Leu Lys His Thr Val Ile Cys Asp Gly
  1               5                  10                  15

Phe Pro Asp Cys Pro Asp Tyr Met Asp Glu Lys Asn Cys
             20                  25

<210> SEQ ID NO 30
<211> LENGTH: 29
<212> TYPE: PRT
<213> ORGANISM: Homo sapiens

<400> SEQUENCE: 30

Glu Cys Ala Asn His Ala Cys Val Ser Arg Asp Leu Trp Cys Asp Gly
  1               5                  10                  15

Glu Ala Asp Cys Ser Asp Ser Ser Asp Glu Trp Asp Cys
             20                  25

<210> SEQ ID NO 31
<211> LENGTH: 232
<212> TYPE: PRT
<213> ORGANISM: Homo sapiens

<400> SEQUENCE: 31

Arg Ile Val Gly Gly Thr Asn Ser Ser Trp Gly Glu Trp Pro Trp Gln
  1               5                  10                  15

Val Ser Leu Gln Val Lys Leu Thr Ala Gln Arg His Leu Cys Gly Gly
             20                  25                  30

Ser Leu Ile Gly His Gln Trp Val Leu Thr Ala Ala His Cys Phe Asp
         35                  40                  45

Gly Leu Pro Leu Gln Asp Val Trp Arg Ile Tyr Ser Gly Ile Leu Asn
     50                  55                  60

Leu Ser Asp Ile Thr Lys Asp Thr Pro Phe Ser Gln Ile Lys Glu Ile
 65                  70                  75                  80

Ile Ile His Gln Asn Tyr Lys Val Ser Glu Gly Asn His Asp Ile Ala
                 85                  90                  95
```

-continued

```
Leu Ile Lys Leu Gln Ala Pro Leu Asn Tyr Thr Glu Phe Gln Lys Pro
            100                 105                 110

Ile Cys Leu Pro Ser Lys Gly Asp Thr Ser Thr Ile Tyr Thr Asn Cys
            115                 120                 125

Trp Val Thr Gly Trp Gly Phe Ser Lys Glu Lys Gly Glu Ile Gln Asn
130                 135                 140

Ile Leu Gln Lys Val Asn Ile Pro Leu Val Thr Asn Glu Glu Cys Gln
145                 150                 155                 160

Lys Arg Tyr Gln Asp Tyr Lys Ile Thr Gln Arg Met Val Cys Ala Gly
                165                 170                 175

Tyr Lys Glu Gly Gly Lys Asp Ala Cys Lys Gly Asp Ser Gly Gly Pro
            180                 185                 190

Leu Val Cys Lys His Asn Gly Met Trp Arg Leu Val Gly Ile Thr Ser
            195                 200                 205

Trp Gly Glu Gly Cys Ala Arg Arg Glu Gln Pro Gly Val Tyr Thr Lys
210                 215                 220

Val Ala Glu Tyr Met Asp Trp Ile
225                 230

<210> SEQ ID NO 32
<211> LENGTH: 232
<212> TYPE: PRT
<213> ORGANISM: Homo sapiens

<400> SEQUENCE: 32

Lys Ile Val Gly Gly Ser Asn Ala Lys Glu Gly Ala Trp Pro Trp Val
1               5                   10                  15

Val Gly Leu Tyr Tyr Gly Gly Arg Leu Leu Cys Gly Ala Ser Leu Val
            20                  25                  30

Ser Ser Asp Trp Leu Val Ser Ala Ala His Cys Val Tyr Gly Arg Asn
            35                  40                  45

Leu Glu Pro Ser Lys Trp Thr Ala Ile Leu Gly Leu His Met Lys Ser
        50                  55                  60

Asn Leu Thr Ser Pro Gln Thr Val Pro Arg Leu Ile Asp Glu Ile Val
65                  70                  75                  80

Ile Asn Pro His Tyr Asn Arg Arg Lys Asp Asn Asp Ile Ala Met
                85                  90                  95

Met His Leu Glu Phe Lys Val Asn Tyr Thr Asp Tyr Ile Gln Pro Ile
            100                 105                 110

Cys Leu Pro Glu Glu Asn Gln Val Phe Pro Pro Gly Arg Asn Cys Ser
            115                 120                 125

Ile Ala Gly Trp Gly Thr Val Val Tyr Gln Gly Thr Thr Ala Asn Ile
130                 135                 140

Leu Gln Glu Ala Asp Val Pro Leu Leu Ser Asn Glu Arg Cys Gln Gln
145                 150                 155                 160

Gln Met Pro Glu Tyr Asn Ile Thr Glu Asn Met Ile Cys Ala Gly Tyr
                165                 170                 175

Glu Glu Gly Gly Ile Asp Ser Cys Gln Gly Asp Ser Gly Gly Pro Leu
            180                 185                 190

Met Cys Gln Glu Asn Asn Arg Trp Phe Leu Ala Gly Val Thr Ser Phe
            195                 200                 205

Gly Tyr Lys Cys Ala Leu Pro Asn Arg Pro Gly Val Tyr Ala Arg Val
210                 215                 220

Ser Arg Phe Thr Glu Trp Ile Gln
225                 230
```

```
<210> SEQ ID NO 33
<211> LENGTH: 221
<212> TYPE: PRT
<213> ORGANISM: Homo sapiens

<400> SEQUENCE: 33

Lys Ile Val Gly Gly Tyr Asn Cys Glu Glu Asn Ser Val Pro Tyr Gln
  1               5                  10                  15

Val Ser Leu Asn Ser Gly Tyr His Phe Cys Gly Gly Ser Leu Ile Asn
             20                  25                  30

Glu Gln Trp Val Val Ser Ala Gly His Cys Tyr Lys Ser Arg Ile Gln
         35                  40                  45

Val Arg Leu Gly Glu His Asn Ile Glu Val Leu Glu Gly Asn Glu Gln
     50                  55                  60

Phe Ile Asn Ala Ala Lys Ile Ile Arg His Pro Gln Tyr Asp Arg Lys
 65                  70                  75                  80

Thr Leu Asn Asn Asp Ile Met Leu Ile Lys Leu Ser Ser Arg Ala Val
                 85                  90                  95

Ile Asn Ala Arg Val Ser Thr Ile Ser Leu Pro Thr Ala Pro Pro Ala
                100                 105                 110

Thr Gly Thr Lys Cys Leu Ile Ser Gly Trp Gly Asn Thr Ala Ser Ser
            115                 120                 125

Gly Ala Asp Tyr Pro Asp Glu Leu Gln Cys Leu Asp Ala Pro Val Leu
        130                 135                 140

Ser Gln Ala Lys Cys Glu Ala Ser Tyr Pro Gly Lys Ile Thr Ser Asn
145                 150                 155                 160

Met Phe Cys Val Gly Phe Leu Glu Gly Gly Lys Asp Ser Cys Gln Gly
                165                 170                 175

Asp Ser Gly Gly Pro Val Val Cys Asn Gly Gln Leu Gln Gly Val Val
            180                 185                 190

Ser Trp Gly Asp Gly Cys Ala Gln Lys Asn Lys Pro Gly Val Tyr Thr
        195                 200                 205

Lys Val Tyr Asn Tyr Val Lys Trp Ile Lys Asn Thr Ile
    210                 215                 220

<210> SEQ ID NO 34
<211> LENGTH: 242
<212> TYPE: PRT
<213> ORGANISM: Homo sapiens

<400> SEQUENCE: 34

Arg Ile Leu Gly Gly Arg Thr Ser Arg Pro Gly Arg Trp Pro Trp Gln
  1               5                  10                  15

Cys Ser Leu Gln Ser Glu Pro Ser Gly His Ile Cys Gly Cys Val Leu
             20                  25                  30

Ile Ala Lys Lys Trp Val Leu Thr Val Ala His Cys Phe Glu Gly Arg
         35                  40                  45

Glu Asn Ala Ala Lys Trp Lys Val Val Leu Gly Ile Asn Asn Leu Asp
     50                  55                  60

His Pro Ser Val Phe Met Gln Thr Arg Phe Val Lys Thr Ile Ile Leu
 65                  70                  75                  80

His Pro Arg Tyr Ser Arg Ala Val Val Asp Tyr Asp Ile Ser Ile Val
                 85                  90                  95

Glu Leu Ser Glu Asp Ile Ser Glu Thr Gly Tyr Val Arg Pro Val Cys
                100                 105                 110
```

-continued

```
Leu Pro Asn Pro Glu Gln Trp Leu Glu Pro Asp Thr Tyr Cys Tyr Ile
        115                 120                 125

Thr Gly Trp Gly His Met Gly Asn Lys Met Pro Phe Lys Leu Gln Glu
        130                 135                 140

Gly Glu Val Arg Ile Ile Ser Leu Glu His Cys Gln Ser Tyr Phe Asp
145                 150                 155                 160

Met Lys Thr Ile Thr Thr Arg Met Ile Cys Ala Gly Tyr Glu Ser Gly
                165                 170                 175

Thr Val Asp Ser Cys Met Gly Asp Ser Gly Gly Pro Leu Val Cys Glu
            180                 185                 190

Lys Pro Gly Gly Arg Trp Thr Leu Phe Gly Leu Thr Ser Trp Gly Ser
        195                 200                 205

Val Cys Phe Ser Lys Val Leu Gly Pro Gly Val Tyr Ser Asn Val Ser
        210                 215                 220

Tyr Phe Val Glu Trp Ile Lys Arg Gln Ile Tyr Ile Gln Thr Phe Leu
225                 230                 235                 240

Leu Asn
```

CORIN, A SERINE PROTEASE

This application is a 371 filing of International Application No. PCT/EP99/03895, filed Jun. 4, 1999 and claims priority to U.S. application Ser. No. 09/314,967, filed May 20, 1999 (converted to Provisional Application No. 60/219, 329), which is a continuation-in-part of U.S. Ser. No. 09/092,029, filed Jun. 5, 1998 (converted to Provisional Application No. 60/367,347, the entire disclosure of each application is hereby incorporated in its entirety by reference.

BACKGROUND OF THE INVENTION

Serine proteases participate in a variety of developmental and physiological processes (Stroud R. *Sci. Am.* 231:74–88, 1974: Neurath H. *Science* 224:350–357, 1984). For instance, serine proteases are involved in cell signaling, cell differentiation, and the conversion of pro-hormones to biologically-active forms. See, e.g., Hong and Hashimoto. *Cell.* 82:785–794, 1995: Inagami. *J. Biol. Chem.*, 264:3043–3046, 1989.

DESCRIPTION OF THE INVENTION

The present invention relates to nucleic acids, polypeptides and fragments thereof, of a novel gene, e.g., a serine protease especially a mammalian serine protease, such as human and mouse corin which contains one or more frizzled, LDLR, scavenger receptor cysteine-rich repeats, and serine protease catalytic domains. The invention further relates to methods of using such nucleic acids and polypeptides in therapeutics, diagnostics, and research. For example, the nucleic acids and polypeptides of corin can be utilized in methods to identify modulators of its activity and in animal models to mimic human disease, and in the diagnosis of pathological conditions.

BRIEF DESCRIPTION OF THE DRAWINGS

Seq. 1 shows a nucleotide sequence for human corin.

Seq. 2 shows a deduced amino acid sequence of human corin.

Seq. 3 shows a nucleotide sequence for mouse corin.

Seq. 4. shows a deduced amino acid sequence for mouse corin.

Figure 1:
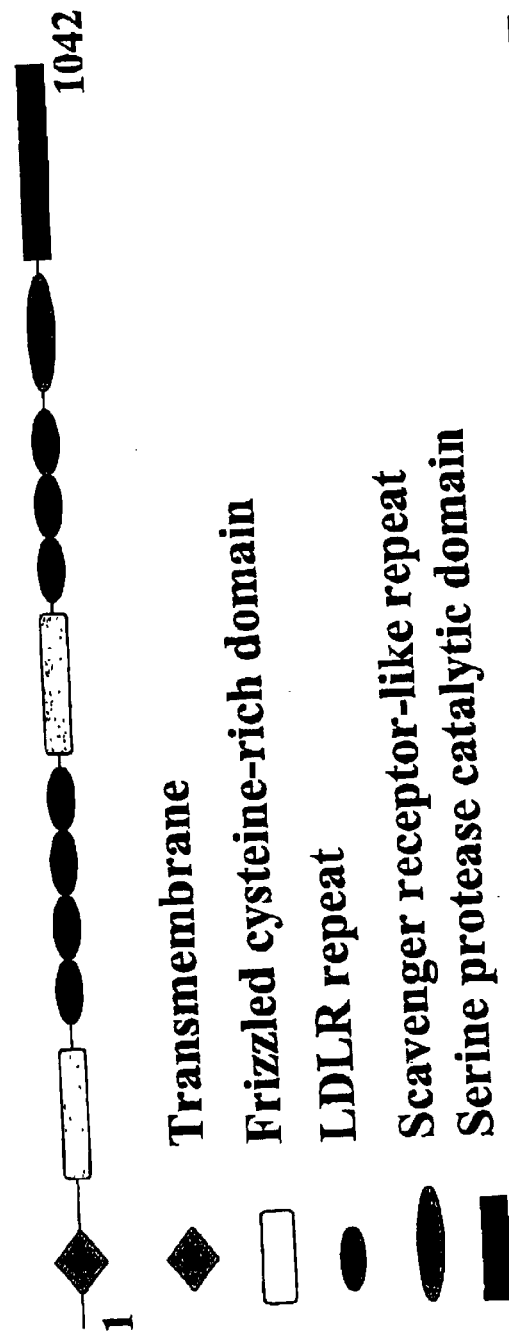
Figure 1:
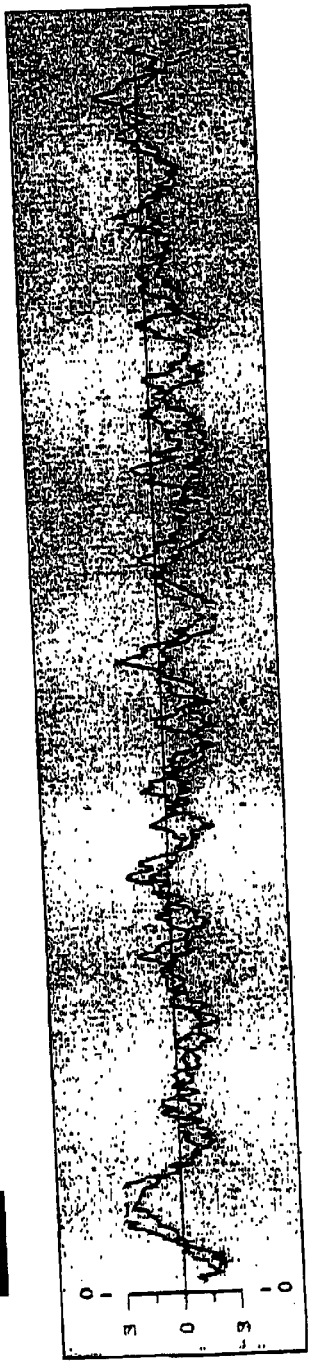

FIG. 1 is a schematic illustrating the arrangement of functional domains within a human corin polypeptide.

FIG. 2 shows an amino acid alignment of frizzled ("Corin Crd1" (SEQ ID NO:22) and "Corin Crd2" (SEQ ID NO:23)) domain from a human corin polypeptide with Frizzled (SEQ ID NO:19), Fz-1 (SEQ ID NO:20) and lin-17 (SEQ ID NO:21).

FIG. 3 shows an amino acid sequence alignment of LDLR-repeats (SEQ ID NOS:24–30, respectively in order of appearance) identified within a human corin polypeptide with a consensus sequence for human LDLR.

FIG. 4 shows an amino acid sequence alignment of a human corin serine protease domain ("Corin") (SEQ ID NO:34) with serine protease domains present in three other proteins. KAL is kalkrein (SEQ ID NO:31). ENTK is enterokinase (SEQ ID NO:32). TRP1 is trypsin (SEQ ID NO:33).

DETAILED DESCRIPTION OF THE INVENTION

Nucleic acid and polypeptide sequences have been identified which code for corin, a novel gene comprising a transmembrane/signal peptide, frizzled domains, low density liprotein receptor repeats (LDLR), scavenger receptor cysteine-rich repeats (SRCR), and a serine protease catalytic domain. See, e.g., FIG. 1.

In accordance with the present invention, a corin polypeptide has an immunogenic activity which is specific for corin; or, an amino acid sequence which is obtainable from a naturally-occurring source and which has one or more of the following activities or domains; a serine protease catalytic activity; a serine protease catalytic activity domain; a serine protease binding substrate activity; a pro-atrial natriuretic factor (ANF) converting enzyme catalytic activity; a frizzled domain; a LDLR repeat domain; and scavenger receptor cysteine-rich repeats (SRCR).

Preferably, the polypeptide fragments coded for by the following nucleic acid fragments from the Unigene database [PubEST] are excluded: Hs.62794 (AA126468 [1686098], AA126648 [1686206], AA625395 [2537780], AA046682 [1524579]. AA249850 [1881137], and AA046793 [15246911], and Hs.71798 (AA147031 [1716421]). (The bracketed numbers refer to the PubEST database.) Optionally tie following fragments can also be excluded: Hs.121626 (AA771958), Hs.1657 (M69297), and Hs.47712 (AA203291), g1231787; g1312726; g1337948; and g942724. The nucleotide sequences of the aforementioned nucleic acids can be identified be searching publicly available databases. However, polypeptides which contain or comprise these sequences are not excluded, e.g., full-length corin, a polypeptide having two or more of these mentioned fragments, or a polypeptide having one of the mentioned fragments and additional amino acid sequences, either from corin or from another source.

By the term "immunogenic activity specific for corin," it is meant that the corin polypeptide elicits an immunological response which is selective for corin. Such response can be cellular or humoral. Thus, the stimulation of antibodies. T-cells, macrophages, B-cells, dendritic cells, etc., by a corin amino acid sequence selected from a mammalian corin polypeptide, e.g., human or mouse corin as shown in Seqs. 2 and 4, is a specific immunogenic activity. These responses can be measured routinely. See also, discussion below on antibodies specific-for corin.

Serine protease catalytic activity means, e.g., that the corin polypeptide possesses a polypeptide cleavage activity, preferably at a peptide bond, e.g., where a serine residue of corin participates in the cleavage of the peptide bond. See, e.g., Stroud. *Sci. Am.,* 231:74–88, 1974; Kraut, *Ann. Rev. Biochem.,* 46:331–358, 1977. The entire corin polypeptide sequence shown in Seq. 2 or Seq. 4, or a part of it, can possess serine protease catalytic activity. Cleavage after amino acid position 801 of Seq. 2 (splitting the peptide bond between arginine and isoleucine) can increase or enhance such catalytic activity, resulting in the release of a catalytic fragment comprising, or consisting essentially of, amino acid positions 802–1042.

A "serine protease catalytic activity domain" refers to a region of a polypeptide which is capable of serine protease catalytic activity, as described above, but which does not necessarily possess complete, if any, activity in the background in which it is present. For instance, members of the trypsin family are often initially expressed as a pro-enzyme which exhibits complete activity only upon cleavage at a specific site within the polypeptide. Cleavage results in release of a proteolytic fragment.

Generally, the "released fragment" is held in place by disulfide bonds with the remaining portion of the protein.

See, Seq. 2, e.g., for cysteines which could form the disulfide bonds. A serine protease catalytic domain refers to the proteolytic fragment prior to its release from the complete corin sequence.

A "pro-atrial natriuretic factor (ANF) converting enzyme catalytic activity" means, e.g., a catalytic activity in which pro-ANF is converted by proteolytic cleavage into one or more smaller peptides. See, e.g., Inagami. *J. Biol. Chem.*, 264:3043–3046, 1989; Rosenzweig and Seidman, *Ann. Rev. Biochem.*, 60:229–255, 1991; Wilkins et al., *Lancet*, 349:1307–1310, 1997. ANF (also, known as ANP) is a cardiac hormone that, e.g., regulates body fluid homeostasis, blood pressure, plasma volume, and other physiological processes involved in heart and kidney function. Other substrates for the convening activity, can also include homologs and proteins homologous to ANF, such as BNP and CNP. See, e.g., Wilkins et al., *Lancet*, 349:1307–1310, 1997; Levin et al., *New Eng. J Med.*, 339: 321–328, 1998. The converting activity can be measured conventionally, e.g., as described in the examples where cleavage of pro-ANF is assayed by detecting a difference in molecular weight of pro-ANF before and after treatment with corin, or with a biologically-active fragment of corin. Since corin can be expressed on the cell-surface, intact cells can be used to process substrates, such as pro-ANF.

Substrate binding is generally considered the first step in enzyme catalysis because the substrate, acting as a ligand, must first attach to the enzyme surface to enable the enzyme to carry out its catalytic reactions. This enzyme surface can be referred to as the active site of the enzyme. Binding of the substrate to the enzyme surface can involve multiple interactions with the enzyme, e.g., chemical bonding with one or more amino acids and/or functional groups which comprise the enzyme. A serine protease substrate binding activity as used herein means that a substrate, e.g., (H-D-Pro-Phe-Arg-pNA.2HCl), S2444 (pyroGlu-Gly-Arg-pNA.HCl), and S2288 (H-D-Ile-Pro-Arg-pNA.2HCl), respectively, or pro-ANF, attaches specifically to a surface of a corin polypeptide. Attachment to the enzyme can be accomplished by one or more of the interactions which hold its naturally-occurring substrate to it: however, a polypeptide can have a substrate binding activity when it holds the substrate with less than the naturally-occurring number and quality of interactions. A serine protease substrate binding activity can optionally be effective: to achieve catalysis of the substrate, to competitively or noncompetitively bind to the active site, to irreversibly attach to the enzyme, to result in the loss of catalytic activity (e.g., where it is a suicide substrate), etc.

Serine protease substrate binding activity can be measured conventionally. For instance, a competition binding assay can be employed to identify substrates which attach to a polypeptide, or derivative thereof, e.g., by combining under effective conditions, a substrate containing a detectable marker, a human corin polypeptide, or fragments thereof, and a compound which is to be tested for substrate binding activity.

The assay can be accomplished in liquid phase, where bound and free substrate are separated by a membrane, or, it can be accomplished in solid phase, as desired. Solid-phase assays can be performed using high-throughput procedures, e.g., on chips, wafers, etc. Substrate binding and catalytic activity can be dissociated from each other. Thus, a corin polypeptide can possess substrate binding activity but not a catalytic activity.

A corin polypeptide can also comprise a "frizzled-like cysteine rich domain" (or "frizzled domain", as used herein) having Wnt binding activity. A frizzled domain can possess a ligand binding activity or region, e.g., as defined and described in Zorn, *Current Biology*, 7:R501–R504, 1997. For example, a frizzled domain can act as a receptor for ligands having homology to Wnts and other secreted glycoproteins involved in cell proliferation, cell signaling, etc. It can be membrane bound or soluble.

In a soluble form, it can also act as antagonist, e.g., when the free frizzled domain of corin binds the free ligand and prevents it from interacting with its cognate receptor on the cell surface.

An LDLR repeat contains a human LDLR consensus sequence as shown in FIG. 7 and can optionally have ligand binding activity.

A corin polypeptide can also comprise a scavenger receptor cysteine-rich repeat domain ("SRCR"). See, e.g., Matsumoto et al, *Proc. Natl. Acad. Sci.*, 87:9133–9137, 1990.

A mammalian corin is a mammalian polypeptide having an amino acid sequence which is obtainable from a natural source and the mentioned activities. It can be full-length (i.e., as shown in Seq. 2) or it can be less than full-length and possess one or more of the mentioned activities. It therefore includes naturally-occurring normal, mutant, polymorphic, etc., sequences. Natural sources include, e.g., living cells, e.g., obtained from tissues or whole organisms, cultured cell lines, including primary and immortalized cell lines, biopsied tissues, etc.

The present invention also relates to fragments of a full-length mammalian corin, such as human or mouse corin. The fragments are preferably "biologically active". By "biologically active", it is meant that the polypeptide fragment possesses an activity in a living system or with components of a living system. Biological activities include those mentioned, e.g., a catalytic activity, a substrate binding activity, and/or an immunogenic activity. Fragments can be prepared according to any desired method, including, chemical synthesis, genetic engineering, cleavage products, etc. See, below.

The present invention also relates to a human corin having a deduced sequence of amino acids 1 to 1042 amino acids as shown in Seq. 2. The 1042 amino acid polypeptide has a predicted molecular weight of about 116 kilodaltons. It comprises the following domains: hydrophobic region at about amino acid positions 46–66; frizzled cysteine-rich domains at about amino acid positions 134–259 and 450–573; seven LDLR repeats at about amino acid positions 268–415 and 579–690; a cysteine-rich region at about amino acid positions 713–801 homologous to a macrophage scavenger receptor motif and a serine protease catalytic domain at about amino acid positions 802–1042. There are nineteen putative N-glycosylation sites present in the extracellular domain which is at about amino acid positions 67–1042.

A corin polypeptide of the invention, e.g., having an amino acid sequence as shown in Seq. 2 or Seq. 4, can by analyzed by available methods to identify other structural and/or functional domains in the polypeptide. For example, a corin polypeptide can be analyzed by methods disclosed in, e.g., Kyte and Doolittle, *J. Mol. Bio.*, 157:105, 1982; EMBL Protein Predict; Rost and Sander, *Proteins*, 19:55–72. 1994.

The hydrophobic domains at about amino acids 46–66 of a human corin can serve as a membrane anchoring sequence. See, also, hepsin, a mammalian serine protease of the trypsin family which contains a transmembrane domain near its amino-terminus (Kurachi et al., *Methods in Enzymology* 244:100–114, 1994); Stubble-stubbloid, a *Drosophila mela-*

*nogaster* serine protease which also contains a transmembrane domain (Appel et al., *Proc. Natl. Acad. Sci. USA* 90:4937–4941, 1993). There are positively charged amino acid residues immediately preceding the hydrophobic and putative transmembrane domain, indicating that corin may be a type II transmembrane protein with the amino terminus in the cytosol.

Corin also contains at least two cysteine-rich frizzled domains at about amino acid positions 134–259 and 450–573. FIG. 2 shows a comparison of the human corin frizzled domains with FZ-1, lin-17, and Frizzled. The frizzled domain comprises, e.g., a ligand binding site. See, e.g., Zorn, *Current Biology*, 7:R501–R504, 1997; Leyns et al., *Cell*, 88:747–756, 1997. As described below, an aspect of the invention is to identify ligands which bind to the corin frizzled domains, and which optionally regulate the activity of cells expressing the corin polypeptide or cells expressing the ligand.

Analysis of the corin protein sequence showed that in the extracellular region there are two frizzled-like cysteine-rich domains, seven LDL receptor repeats, one macrophage scavenger receptor-like domain, and one trypsin-like serine protease domain (2A). Two frizzled-like cysteine-rich domains are located at amino acids 134–259 and 450–573, respectively. Amino acid sequences of these two domains share significant similarities with the extracellular cystein-rich domain of the Drosophila Frizzled protein, a seven transmembrane receptor essential for polarity determination during the development of the fruitfly (19). The frizzled-like cysteine-rich domains have also been found in other proteins, such as Dfz2 in Drosophila (20), Lin-17 in C. elegans (21) and FZ-1 in human (22). The sequences of the two frizzled-like cysteine-rich domains in corin are closest to those in Lin-17 and FZ-1. All the ten conserved cysteine residues are present in the frizzled-like cysteine-rich domains of corin.

Between amino acids 268–415 and 579–690, there are seven cysteine-rich repeats homologous to the LDL receptor class A repeats (23). Each repeat is about 36 amino acids long and contains six cysteine residues as well as a highly conserved cluster of negatively charged amino acids. In the LDL receptor, these cysteine-rich repeats bind calcium ions and play an essential role in endocytosis of the extracellular ligands (23). Similar motifs have been found in the extracellular domain of other membrane receptors, such as LDL receptor-related protein (LRP1) (24), megalin (also known as LRP2 or gp330) (25), complement proteins (26), enterokinase (27), and Drosophila proteins yolkless and nude1 (28,29).

In addition to the frizzled-like cysteine-rich domains and LDL receptor-like repeats, there is another cysteine-rich region between amino acids 713 and 801 in corin. This region contains 88 amino acids and is homologous to the cysteine-rich motif found in the macrophage scavenger receptor (30). This motif is also present in the sea urchin spermatozoa speract receptor (31,32) and the vertebrate serine protease, enterokinase (27).

At the carboxyl terminus of corin protein between amino acid residues 802 and 1042, there is a trypsin-like serine protease domain. This protease domain is highly homologous to the catalytic domain of members of the trypsin superfamily. For example, amino acid sequence identities between corin and prekallikrein (33), factor XI (34) and hepsin (35) are 40%, 40% and 38%, respectively. All essential features of serine protease sequences are well conserved in corin. The active site residues of the catalytic triad are located at His843, Asp892 and Ser985. The amino acid residues forming the substrate specificity pocket are located at Asp979, Gly1007 and Gly1018. These residues are predicted to bind the substrate P1 residues, suggesting that corin would cleave its substrate after basic residues, such as lysine or arginine. In addition, a putative activation cleavage site was found at Arg801, suggesting that corin would be synthesized as an inactive zymogen and that another trypsin-like enzyme was required for its activation.

In the protease domain, there are 12 cysteine residues. Potential pairing of these cysteine residues can be predicted by comparing with other well-studied serine proteases, such as trypsin and chymotrypsin. First three pairs of cysteine residues present in essentially all members of the trypsin superfamily are located at Cys828–Cys844, Cys955–Cys970 and Cys981–Cys1010. Two more pairs of cysteine residues are present at the positions Cys790–Cys912 and Cys926–Cys991. These two pairs of cysteine residues are commonly found in a subfamily of two-chain serine proteases, such as chymotrypsin and prekallikrein (33). The presence of Cys790 and Cys912 indicated that after the activation cleavage at Arg801, the catalytic domain of corin would remain attached to the rest of molecule by a disulfide bond. Interestingly, there is one additional pair of cysteine residues, Cys817 and Cys830, present in corin. Cysteine residues at these two positions were not found in any other serine proteases in vertebrates. A search of databases showed that a chymotrypsinogen-like serine protease from the lugworm, Arenicola marina, had two cysteine residues at the corresponding positions (36). A model of the corin protease domain was built based on the structure of bovine chymotrypsinogen A. Based on this corin model, where the Cα atoms of these two cysteine residues were held fixed during energy minimization, the distance between the sulfur atoms of their side chains is about 2.5 Å after rotamer searching. The model indicates that these two cysteines are likely to form a disulfide bond connecting two b-sheets in the core of the protease domain.

In addition to the human corin sequence, a corin from another mammalian species, mouse, has been cloned and identified. A full-length nucleotide and amino acid sequence of mouse corin is shown in Seqs. 3 and 4. There are 1113 amino acids in the mouse corin and it comprises the same domains as human corin. There is 89% amino acid sequence identity between mouse and human corin.

Other corin homologs from mammalian and non-mammalian sources can be obtained according to various methods. For example, hybridization with an oligonucleotide selective for a mammalian corin can be employed to select such homologs, e.g., as described in Sambrook et al., *Molecular Cloning*, 1989, Chapter 11. Such homologs can have varying amounts of nucleotide and amino acid sequence identity and similarity to corin. Non-mammalian organisms include, e.g., vertebrates, invertebrates, zebra fish, chicken, Drosophila, *C. elegans*, Xenopus, *S, pombe*, *S. cerevisiae*, roundworms, prokaryotes, plants, Arabidopsis, viruses, etc.

The invention also relates to corin specific amino acid sequences, e.g., a defined amino acid sequence which is found in the particular human or mouse sequences of Seqs. 2 and 4, but not in other amino acid sequences from non-corin polypeptides. A specific amino acid sequence can be found routinely, e.g., by searching a gene/protein database using the BLAST set of computer programs. A corin specific amino acid sequence can be useful to produce peptides as antigens to generate an immune response specific for it. Antibodies obtained by such immunization can be used as a specific probe for a mammalian corin protein for diagnostic or research purposes.

As mentioned, polypeptides of the present invention can comprise a complete coding sequence for a corin, or fragments thereof. Useful fragments include, e.g., fragments comprising, or consisting essentially, of the frizzled domain, one or more LDLR domains, SRCR repeats the transmembrane domain, the serine catalytic domain or fragment. A preferred fragment of human corin comprises the polypeptide sequence of Seq. 2, with the proviso that the fragment is not a polypeptide coded for by Hs.62794 (AA126468 [1686098], AA126648 [1686206], AA625395 [2537780], AA046682 [1524579], AA249850 [1881137], and AA046793 [1524691]), and Hs.71798 (AA147031 [1716421]). See, above.

A fragment of a corin polypeptide can be selected to have a specific biological activity, e.g., a serine protease activity, a pro-ANF converting enzyme activity, a substrate binding activity, an immunogenic activity, etc. A useful fragment can be identified routinely by testing such fragments for a desired activity. The measurement of these activities is described below and in the examples. These peptides can also be identified and prepared as described in EP 496 162.

A polypeptide of the present invention can also have 100% or less amino acid sequence identity to the amino acid sequence set forth in Seq. 2 or 4. For the purposes of the following discussion: Sequence identity means that the same nucleotide or amino acid which is found in the sequence set forth in Seqs. 1–4 is found at the corresponding position of the compared sequence(s). A polypeptide having less than 100% sequence identity to the amino acid sequence set forth in Seq. 2 or Seq. 4 can contain various substitutions from the naturally-occurring sequence, including homologous and non-homologous amino acid substitutions. See below for examples of homologous amino acid substitution. The sum or the identical and homologous residues divided by the total number of residues in the sequence over which the corin polypeptide is compared is equal to the percent sequence similarity. For purposes of calculating sequence identity and similarity, the compared sequences can be aligned and calculated according to any desired method, algorithm, computer program, etc., including, e.g., FASTA, BLASTA. A polypeptide having less than 100% amino acid sequence identity to the amino acid sequence of Seq. 2 or Seq. 4 can comprise e.g., about 99%, 98%, 97%, 95%, 90%, 70% etc. A preferred amount of amino acid sequence identity is about 85% or more, e.g., about 86%.

A mammalian corins polypeptide, fragment, or substituted polypeptide can also comprise various modifications, where such modifications include lipid modification, methylation, phosphorylation, glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

Polypeptides of the present invention (e.g., human corin or mouse corin, fragments thereof, mutations thereof) can be used in various ways, e.g., in assays, as immunogens for antibodies as described below, as biologically-active agents (e.g., having one or more of the activities associated with corin).

A polypeptide coding for a corin, a derivative thereof, or a fragment thereof, can be combined with one or more structural domains, functional domains, detectable domains, antigenic domains, and/or a desired polypeptide of interest, in an arrangement which does not occur in nature, i.e., not naturally-occurring, e.g., as in a human or murine corin gene, a genomic fragment prepared from the genome of a living organism, e.g., an animal, preferably a mammal, such as human, mouse, or cell lines thereof. A polypeptide comprising such features is a chimeric or fusion polypeptide. Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous (e.g., with multiple N-terminal domains to stabilize or enhance activity) or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as catalytic, signalling, growth promoting, cellular targeting (e.g., signal sequence, targeting sequence, such as to endosomes, lysosomes, ER, nucleus), etc., a structural function such as hydrophobic, hydrophilic, membrane-spanning, etc., receptor-ligand functions, and/or detectable functions, e.g., combined with enzyme, fluorescent polypeptide. green fluorescent protein, (Chalfie et al., 1994, *Science*, 263:802; Cheng et al., 1996, *Nature Biotechnology*, 14:606; Levy et al., 1996, *Nature Biotechnology*, 14:610, etc. In addition, a polypeptide, or a part of it, can be used as a selectable marker when introduced into a host cell. For example, a nucleic acid coding for an amino acid sequence according to the present invention can be fused in frame to a desired coding sequence and act as a tag for purification, selection, or marking purposes. The region of fusion can encode a cleavage site to facilitate expression, isolation, purification, etc.

A polypeptide according to the present invention can be produced in an expression system, e.g., in vivo, in vitro, cell-free, recombinant, cell fusion, etc., according to the present invention. Modifications to the polypeptide imparted by such systems include glycosylation, amino acid substitution (e.g., by differing codon usage), polypeptide processing such as digestion, cleavage, endopeptidase or exopeptidase activity, attachment of chemical moieties, including lipids and phosphates, etc.

A polypeptide according to the present invention can be recovered from natural sources, transformed host cells (culture medium or cells) according to the usual methods, including, detergent extraction (e.g., Triton-X-100 CHAPS, octylglucoside), ammonium sulfate or ethanol precipitation, acid extraction, anion or cation exchange chromatography, phosphocellulose chromatography, hydrophobic interaction chromatography, hydroxyapatite chromatography and lectin chromatography. Protein refolding steps can be used, as necessary, in completing the configuration of the mature protein. Finally, high performance liquid chromatography (HPLC) can be employed for purification steps. A corin polypeptide can also be isolated as described for other serine proteases, e.g., Wu et al., *J Biol. Chem.*, 267: 24408–24412, 1992; Wu et al., *Proc. Natl. Acad. Sci.*, 88:6775–6779, 1991.

A mammalian corin nucleic acid, or fragment thereof, is a nucleic acid having a nucleotide sequence obtainable from a natural source. See, above. It therefore includes naturally-occurring, normal, mutant, polymorphic alleles, degenerate sequences, etc. Natural sources include, e.g., living cells obtained from tissues and whole organisms, cultured cell lines, including primary and immortalized cell lines. Preferably, the following nucleic acid fragments from the Unigene database [PubEST] are excluded: Hs.62794

(AA126468 [1686098], AA126648 [1686206], AA625395 [2537780], AA046682 [1524579], AA249850 [1881137], and AA046793 [1524691]), and Hs.71798 (AA147031 [1716421]). (The bracketed numbers refer to the PubEST database.) Optionally, the following fragments can also be excluded: Hs.121626 (AA771958), Hs.1657 (M69297), and Hs.47712 (AA203291), g1231787; g1312726; g1337948; and g942724. The nucleotide sequences of the aforementioned nucleic acids can be identified be searching publicly available databases. However, nucleic acids which contain or comprise these sequences are not excluded, e.g., full-length corin, or, a nucleic acid having two or more of these mentioned fragments. It is also preferred that the mentioned fragments in a cloning vector, such as a plasmid or phage, are excluded.

Human corin is expressed as an about a 5 kb mRNA. It is most abundant in heart. It is either absent, or expressed in very low levels in brain, placenta lung, liver, skeletal muscle, kidney, pancreas, spleen, thymus, prostate, testis, ovary small intestine, colon, bladder, uterus, and stomach. Consequently, corin can be used as a marker for the presence of heart tissue, e.g., in tissue sections (using corin-specific antibodies or corin-specific nucleic acid probes), in biopsied samples, etc. Corin was also detected in various human cell lines, including uterus tumor, osteosarcoma, endometrium carcinoma lines HEC-1-A, AN3 CA, and RL95-2, leiomyosarcoma SK-LM-1, and osteosarcoma U2-OS. Further details are described in the examples below.

A nucleic acid sequence of a human corin allele having 4933 base pairs is shown in Seq. 1. The size of the DNA is consistent with the length of corin mRNA (~5 kb) detected by Northern analysis. An ATG codon is located at position 95 that may represent the translation initiation site. The open reading frame (ORF) spans 3126 bp with a 5' untranslated region (UTR) of 94 nucleotides before the initiation codon. At the 3' end, there is a 1.7-kb 3' UTR after the stop codon at position 3221. A polyadenylylation signal of AATAAA is present 12 nucleotides before the poly $(A)^+$ tail. A nucleic acid sequence of the invention can contain the complete coding sequence from amino acid I to amino acid 1042, degenerate sequences thereof, and fragments thereof. A nucleic acid according to the present invention can also comprise a nucleotide sequence which is 100% complementary, e.g., an anti-sense, to any nucleotide sequence mentioned above and below.

The present invention also relates to a mouse nucleotide sequence coding for all or part of a corin, e.g., as shown in Seq. 3. As is the case for the human allele, the invention relates to degenerate sequences thereof, and anti-sense fragments thereof Northern analysis shows a prominent transcript at about 5 kb in samples derived from the heart. In contrast to Northen analysis with human samples, low levels of mRNA were detected in samples obtained from mouse testes and kidneys. In situ hybridization with mouse corin mRNA was also detected in embryonic heart tissue, atrium and ventricular myocytes, developing kidneys, and cartilage-derived structures. Further details are described in the examples.

A nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell at a particular stage of development, having a desired genotype, phenotype (e.g., an embryonic or adult heart cell or tissue), etc.

As described for corin polypeptides mentioned above, a nucleic acid comprising a nucleotide sequence coding for a polypeptide according to the present invention can include only coding sequence; a coding sequence and additional coding sequence (e.g., sequences coding for leader, secretory, targeting, enzymatic, fluorescent or other diagnostic peptides), coding sequences and non-coding sequences, e.g., untranslated sequences at either a 5' or 3' end, or dispersed in the coding sequence, e.g., introns. A nucleic acid comprising a nucleotide sequence coding without interruption for a polypeptide means that the nucleotide sequence contains an amino acid coding sequence for a corin, with no non-coding nucleotides interrupting or intervening in the coding sequence, e.g., absent intron(s). Such a nucleotide sequence can also be described as contiguous. A genomic DNA coding for a mammalian human or mouse corin, etc., can be obtained routinely.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence.

For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids which hybridize to a nucleic acid comprising a nucleotide sequence as set forth in Seq. 1 and Seq. 3. A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in Seq. 1 and Seq. 3. A nucleic acid capable of hybridizing to such sequence, preferably, possesses, e.g., about 85%, more preferably, 90%. 92%, and even more preferably, 95%, 97%, or 100% complementarity, between the sequences. The present invention particularly relates to nucleic acid sequences which hybridize to the nucleotide sequence set forth in Seq. 1 and Seq. 3 under low or high stringency conditions.

Nucleic acids which hybridize to corin sequences can be selected in various ways. For instance, blots (i.e., matrices containing nucleic acid) can be incubated in a prehybridization solution (6×SSC, 0.5% SDS, 100 ug/ml denatured salmon sperm DNA, 5× Denhardt's solution, and 50% formamide), at 30EC. overnight, and then hybridized with radiolabeled probes (corin) in a hybridization solution (6×SSC, 0.5% SDS, 100 ug/ml denatured salmon sperm DNA and 50% formamide), at 42EC overnight in accordance with known procedures. Blots can be washed at high stringency conditions that allow, e.g., for less than 5% bp mismatch (e.g., wash twice in 0.1% SSC and 0.1% SDS for 30 min at 65EC), i.e., 95% or greater sequence identity. Whereas high stringency washes can allow for less than 5% mismatch, relaxed or low stringency wash conditions (e.g., wash twice in 0.2% SSC and 0.5% SDS for 30 min at 37EC) can permit up to 20% mismatch. Another non-limiting example of low stringency conditions includes a final wash at 42EC in a buffer containing 30 mM NaCl and 0.5% SDS. Another non-limiting example of high stringency conditions includes a final wash at 65EC in aqueous buffer containing 30 mM NaCl and 0.5% SDS. Washing and hybridization can also be performed as described in Sambrook et al., *Molecular Cloning*, 1989. Chapter 9. Hybridization can also be based on a calculation of melting temperature (Tm) of the hybrid formed between the probe and its target, as described in Sambrook et al. Such stringent conditions can select sequences which have, e.g., at least about 95%, preferably 97%, nucleotide complementarity between the nucleic acids, with the proviso that such nucleic acid is not: Hs.62794 (AA126468 [1686098], AA126648 [1686206], AA625395 [25377803, AA046682 [1524579], AA249850 (1881137], and AA046793 [1524691]), and Hs.71798 (AA147031 [1716421]). See, also above and below. Nucleic acids which contain or comprise these sequences are not excluded, e.g., full-length corin, or a nucleic acid having two or more of these mentioned fragments.

According to the present invention, a nucleic acid or polypeptide can comprise one or more differences in the nucleotide or amino acid sequence set forth in Seqs. 1–4. Changes or modifications to the nucleotide and/or amino acid sequence can be accomplished by any method available, including directed or random mutagenesis.

A nucleic acid coding for a human or mouse corin according to the invention can comprise nucleotides which occur in a naturally-occurring corin gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtainable from a natural source, e.g., animal tissue and cells, body fluids, tissue culture cells, forensic samples. Naturally-occurring mutations can include deletions (e.g., a truncated amino- or carboxy-terminus), substitutions, or additions of nucleotide sequence. These genes can be detected and isolated by nucleic acid hybridization according to methods which one skilled in the art would know. A nucleotide sequence coding for a human or mouse corin polypeptide of the invention can contain codons found in a naturally-occurring gene, transcript, or cDNA, for example, e.g., as set forth in Seq. 1 or Seq. 3, or it can contain degenerate codons coding for the same amino acid sequences. For instance, it may be desirable to change the codons in the sequence to optimize the sequence for expression in a desired host.

The present invention also relates to corin polypeptide muteins, i.e., any polypeptide which has an amino acid sequence which differs in amino acid sequence from an amino acid sequence obtainable from a natural source (a fragment of a mammal corin does not differ in amino acid sequence from a naturally-occurring corin). Thus, corin muteins comprise amino acid substitutions, insertions, and deletions, including non-naturally occurring amino acids. See, e.g., Wu et al., *Proc. Natl. Acad. Sci.*, 88:7775–6779, 1991, especially reporting amino acid substitutions where a basic amino acid was substituted with glutamic acid, for guidance on making mutations.

Muteins to a corin amino acid sequence of the invention can also be prepared based on homology searching from gene data banks, e.g., Genbank, EMBL. Sequence homology searching can be accomplished using various methods, including algorithms described in the BLAST family of computer programs, the Smith-Waterman algorithm, etc.

A mutein(s) can be introduced into a sequence by identifying and aligning amino acids within a domain which are identical and/or homologous between polypeptides and then modifying an amino acid based on such alignment. For instance, sequence comparisons between human corin and the Frizzled. LDLR, and serine protease domains of other proteins are illustrated in FIGS. 2–4. These alignments reveal amino acid positions which are identical and also amino acid positions where the residues differ from each other but are homologous. Homologous amino acids can be defined based on the size of the side chain and degree of polarization, including, small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine.

Homologous acids can also be grouped as follows: uncharged polar R groups, glycine, serine, threonine, cysteine, tyrosine, asparagine, glutamine; acidic amino acids (negatively charged), aspartic acid and glutamic acid; basic amino acids (positively charged), lysine, arginine, histidine. Homologous amino acids also include those described by Dayhoff in the *Atlas of Protein Sequence and Structure* 5 (1978), and by Argos in *EMBO J.*, 8, 779–785 (1989).

Muteins in accordance with the present invention include amino acid sequences where a residue in the human or mouse corin sequence is replaced by a homologous residue from a corresponding domain.

Thus, the present invention relates to a corin nucleotide sequence of Seq. 2 or 4, wherein said nucleic, acid codes for a polypeptide and one or more amino acid positions are substituted or deleted, or both, and the polypeptide coded for by the nucleic acid has a serine protease catalytic domain activity or an immunogenic activity specific for corin. Such nucleic acid can contain one or more substituted amino acid positions which are substituted by homologous amino acids.

In addition, the sequence alignments as illustrated in FIGS. 2–4 also provide information on amino acid substitutions that would be expected to reduce, decrease, or, eliminate a biological activity. For instance, where alignment reveals identical amino acids conserved between two or more domains (e.g., replacing the conserved H, D, or S residues indicated in FIG. 4), elimination or substitution of the amino acid(s) would affect its biological activity. Mutations in the catalytic triad, namely, His910, Asp959, and Ser1052 (mouse corin), abolish the catalytic activity of serine proteases.

A corin polypeptide mutein, and its corresponding nucleotide coding sequence, can have an amino acid sequence as set forth in Seq. 2 or Seq. 4, except where one or more positions are substituted by homologous amino acids, e.g., where there are 1, 5, 10, 15, or 20 substitutions. The invention also relates to mutein polypeptides and mutein nucleic acids coding for such polypeptides.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide. phosphorothioate, phosphoramidate, methylphosphonate, carbamate, etc., depending on the desired purpose, e.g., resistance to nucleases, such as RNase H, improved in vivo stability, etc. See, e.g., U.S. Pat. No. 5,378.825.

Various modifications can be made to the nucleic acids, such as attaching detectable markers (avidin, biotin, radioactive elements), moieties which improve hybridization, detection, or stability. The nucleic acids can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres. polyacrylamides, etc., according to a desired method. See, e.g., U.S. Pat. Nos. 5.470.967; 5,476,925; 5,478.893.

Another aspect of the present invention relates to oligonucleotides and nucleic acid probes. Such oligonucleotides or nucleic acid probes can be used, e.g., to detect, quantitate, or isolate a mammalian corin nucleic acid in a test sample. In a preferred embodiment, the nucleic acids can be utilized as oligonucleotide probes, e.g., in PCR, in RACE, differential display, in combination with cDNA libraries, expression libraries, etc. Useful oligonucleotides are described below in the examples. Detection can be desirable for a variety of different purposes, including research, diagnostic, and forensic. For diagnostic purposes, it may be desirable to identify the presence or quantity of a such a nucleic acid sequence in a sample, where the sample is obtained from tissue, cells, body fluids, etc. In a preferred method, the present invention relates to a method of detecting a nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR (e.g., Saiki et al., 1988, *Science*, 241:53; U.S. Pat. No. 4,683,202; *PCR Protocols: A Guide to Methods and Applications*, Innis et al., eds., Academic Press, New York, 1990) or differential display (See, e.g., Liang et al., *Nucl. Acid Res.*, 21:3269–3275, 1993; U.S. Pat. No. 5,599,672; WO97/18454) or RACE.

Such detection can be accomplished in combination with oligonucleotides for other genes, e.g., genes involved in cardiac tissue or bone development or function.

Another aspect of the present invention is a nucleotide sequence which is unique to human corin or mouse corin. By a unique sequence to a corin, it is meant a defined order of nucleotides which occurs in corin, e.g., in the nucleotide sequence of Seq. 1 or 3, but rarely or infrequently in other nucleic acids, especially not in an animal nucleic acid, preferably mammal, such as human, rat, mouse, etc. Both sense and antisense nucleotide sequences are included. A unique nucleic acid according to the present invention can be determined routinely. A nucleic acid comprising such a unique sequence can be used as a hybridization probe to identify the presence of, e.g., human or mouse corin, in a sample comprising a mixture of nucleic acids, e.g., on a Northern blot. Hybridization can be performed under stringent conditions (see, above) to select nucleic acids having at least 95% identity (i.e., complementarity) to the probe, but less stringent conditions can also be used. A unique corin nucleotide sequence can also be fused in-frame, at either its 5' or 3' end, to various nucleotide sequences as mentioned throughout the patent, including coding sequences for other parts of corin, enzymes, GFP, etc, expression control sequences, etc.

Hybridization can be performed under different conditions, depending on the desired selectivity, e.g., as described in Sambrook et al., *Molecular Cloning*, 1989. For example, to specifically detect human or mouse corin, an oligonucleotide can be hybridized to a target nucleic acid under conditions in which the oligonucleotide only hybridizes to it, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%.

Oligonucleotides of the present invention can comprise any continuous nucleotide sequence of Seq. 1 or Seq. 3. These oligonucleotides (nucleic acid) according to the present invention can be of any desired size, e.g., about 10–200 nucleotides, 12–100, preferably 12–50, 12–25, 14–16, at least about 15, at least about 20, etc. The oligonucleotides can have non-naturally-occurring nucleotides, e.g., inosine. The oligonucleotides can have 100% identity or complementarity to a sequence of Seq. 1 or Seq. 3, or it can have mismatches or nucleotide substitutions, e.g., 1, 2, 3, 4, or 5 substitutions. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Anti-sense nucleic acid can also be prepared from a nucleic acid according to the present invention, preferably an anti-sense to a coding sequence of Seq. 1 or 3. Antisense nucleic acid can be used in various ways, such as to regulate or modulate expression of corin, e.g., inhibit it, to detect its expression, or for in situ hybridization. These oligonucleotides can be used analogously to U.S. Pat. No. 5,576,208. For the purposes of regulating or modulating expression of corin, an anti-sense oligonucleotide can be operably linked to an expression control sequence.

The nucleic acid according to the present invention can be labeled according to any desired method. The nucleic acid can be labeled using radioactive tracers such as $^{32}$P, $^{35}$S, $^{125}$I, $^{3}$H, or $^{14}$C, to mention some commonly used tracers. The radioactive labeling can be carried out according to any method such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligonucleotides, anti-sense nucleic acid, etc., can be used to detect expression of corin in whole organs. tissues, cells, etc., by various techniques, including Northern blot, PCR, RACE, in situ hybridization, etc. Such nucleic acids can be particularly useful to detect disturbed expression, e.g., cell-specific and/or subcellular alterations, of corin. The levels of corin can be determined alone or in combination with other gene products, especially cardiac specific gene products.

A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medias, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. A nucleic acid can be introduced into the cell by any effective method including, e.g., naked DNA, calcium phosphate precipitation, electroporation, injection. DEAE-Dextran mediated transfection, fusion with liposomes, association with agents which enhance its uptake into cells, viral transfection. A cell into which a nucleic acid of the present invention has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells, e.g., COS-7, CV1, BHK, CHO, HeLa, LTK, NIH 3T3, yeast, insect cells, such as Sf9 (*S. frugipeda*) and Drosophila, bacteria, such as *E. coli, Streptococcus. bacillus*, yeast, fungal cells, plant cells, embryonic stem cells (e.g., mammalian, such as mouse or human), bone cells (such as, osteoclasts or chondrocytes), cardiac cells (e.g., from a primary culture), muscle cells, neuronal cells, etc. Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter. MMTV, SV40; trp, lac, tac, or T7 promoters for bacterial hosts: or alpha factor, alcohol oxidase, or PGH promoters for yeast.

Another gene of interest can be introduced into the same host for purposes of, e.g., modulating corin function. Such genes can be the normal gene, or a variation, e.g., a mutation, chimera, polymorphism, etc.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. A corin cDNA as shown in Seq. 1 can be used as a 4.8 kb molecular weight marker in nucleic acid electrophoresis.

The human corin cDNA as shown in Seq. 1 maps to human chromosome position 4p12–13. It can thus be used as a marker in pedigree mapping. For example, this chromosomal region appears to segregate with total anomalous pulmonary venous return (TAPVR) and therefore could be used to map the disease in association with other genetics markers. See, e.g., Bleyl et al., *Am. J. Hum. Genet.*, 56: 408–415, 1995.

Another aspect of the present invention relates to the regulation of biological pathways in which a corin gene, or gene product, is involved, particularly pathological and developmental conditions, and to the diagnosis of such conditions by detecting either corin polypeptide or nucleic acid. For example, ANF is involved in a variety of physiological processes related to the cardiovascular and kidney systems, including, e.g., body fluid homeostasis, blood pressure, vasodilation, natriuresis, inhibition of sodium absorption in the glomerular duct, increased glomerular filtration, inhibition of aldosterone production and secretion, mitogenesis, etc. The regulation of the pro-ANF converting activity of corin can therefore have profound effects on an organism=s physiology. For instance, ventricular levels of ANF are normally low in ventricular myocytes but increase dramatically with cardiovascular diseases. In patients with congestive heart failure, plasma levels of ANF are high. The high concentrations are correlated with the severity of ventricular dysfunction. Similarly, high concentrations of ANF are associated with cardiac arrhythmias and hemodynamic compromise. See, e.g., Levin et al., *New Engl. J. Med.*, 339:321–328, 1998. Abnormally high levels can be reduced by inhibiting the activity of corin, e.g., transcriptionally by inhibiting gene expression or by administering enzyme inhibitors, which act directly on catalytic activity.

Since corin is highly expressed in cartilage-derived and cardiac cells, it may be involved in diseases associated with these tissues, such as familial hypertrophic cardiomyopathy, osteopetrosis, and osteoporosis-pseudoglioma syndrome, osteoporosis, Paget=s disease, osteitis deformans, and total anomalous pulmonary venous return. As mentioned, corin oligonucleotides can be utilized in pedigree mapping to study the familial inheritance of these diseases, in analogy to TAPVR, and for diagnostic purposes (e.g., prenatal) if corin is associated (gene linkage or causative) with such a disease. Corin may also be involved heart development, developmental pathways which involve signaling with Wnt proteins and other growth factors, cell differentiation (e.g., chondrocyte differentiation), and related processes. In addition corin may be involved in cell-cell signaling, differentiation (bone and/or cardiac), and other developmental pathways. This role may be mediated by serine protease catalytic activity, frizzled domains, and/or the LDRL domains. Corin may also be involved in the processing (e.g., by catalytic cleavage of a progrowth factor) of growth factors, such as BMP or TGF-β.

Along these lines, a further aspect of the invention relates to the treatment of cardiovascular and kidney disease, such as hypertension, congestive heart disease, or renal failure (as well as pathological conditions related to any to other pathway in which corin participates), comprising the administration, to a host in need thereof, of an effective amount of an agent which modulates the activity of a mammalian corin. By the term Amodulates.≅ it is meant: increasing, agonizing, promoting, stabilizing, decreasing, reducing, antagonizing, blocking, inhibiting, etc. The nature of the desired modulatory effect can be determined routinely, e.g., on whether the pathological effect is produced by elevated or diminished quantities of ANF. The activity can be inhibited by administering an agent which directly blocks the catalytic activity of corin (e.g., an enzyme inhibitor, such as leupeptin or diisopropyl fluorophosphate) or by an agent, such as antisense, which blocks transcription or translation of the corresponding gene. Corin activity can be increased, e.g., by administering a corin gene which is effective to produce corin polypeptide. Corin gene can be administered in analogy to other gene therapies. See, e.g., Magovern et al., Hum. Gen. Ther., 8:215–227, 1997; Springer et al., Mol. Cell., 2:549–558, 1998.

The present invention also relates to methods of modulating the activity of corin in any environment, including in vitro and in vivo, either by directly modulating its activity, or by modulating expression of the gene which encodes it. Enzyme activity can be measured conventionally, e.g., as described in Wu et al., J. Biol. Chem., 267:24408–24412, 1992; Wu et al., Proc. Nail. Acad. Sci., 88:6775–6779, 1991. Converting activity can be measured as described in the examples, or, e.g., as described by Inagami, J. Biol. Chem., 264:3043–3046, 1989. The invention thus relates to a method of identifying modulators of the aforementioned activity of a corin polypeptide, fragment, or mutein thereof, comprising: reacting, in the presence of a test compound, a corin polypeptide, a fragment thereof, and a substrate for serine protease or the converting enzyme, under conditions effective for said polypeptide or fragment thereof to cleave said substrate; detecting said cleavage; and identifying whether the test compound modulates said serine protease activity by comparing the amount of cleavage in the presence and absence of the test compound.

Any substrate is suitable, and, any means for detection, such as a chromogenic, fluorogenic, radioactive, electrophorelic, etc, can be utilized. For example, the products of cleavage can be detected using labeled substrates in combination with gel electrophoresis. In a preferred example, the substrate is a chromogenic substrate, i.e., a peptide that reacts with the serine protease and which is designed to possess a selectivity similar to that of the natural substrate for the enzyme. Attached to the peptide part of the chromogenic substrate is a chemical group which when released after the enzyme cleavage gives rise to a detectable color. The color change can be followed spectrophotometrically and is proportional to the proteolytic activity of the serine protease catalytic domain. These substrates can be routinely synthesized. Hydrolysis of substrate (e.g., containing 4-nitroaniline, pNA, as the chromophore) can be measured at room temperature by following absorbance at 405 nm. Substrates which can be used to measure amidolytic activity of serine proteases include, S2302 (H-D-Pro-Phe-Arg-pNA.2HCl), S2444 (pyroGlu-Gly-Arg-pNA.HCl), and S2288 (H-D-Ile-Pro-Arg-pNA.2HCl), respectively. Other chromophores that can be incorporated into the substrate include, e.g., ANBA, ADMP, thiolester derivatives, etc. See, e.g., Chromogenix catalogs and its websites for further information. Values for $K_m$ and $k_{cat}$ can be calculated by the Michaelis-Menton equation.

The invention also relates to a method of identifying compounds which bind specifically to a corin polypeptide, comprising: contacting a corin polypeptide with a test compound under conditions effective for said test compound to bind specifically to said corin polypeptide; and detecting binding to said corin polypeptide. Binding assays can be performed conventionally. The corin polypeptide can comprise the complete coding sequence, or fragments thereof, especially, one or more LDLR domains, frizzled domains. SRCR, or combinations thereof. See, above, for amino acid positions of such domains. The domains can be utilized as fusion proteins, e.g., in combination with immunoglobulin domains. See, e.g., U.S. Pat. No. 5,639,597.

The corin component can be added to the reaction mixture in a variety forms, e.g., substantially purified, as a component of a cell, as a soluble extract, or as a lysate. In each case, the corin polypeptide can be obtained from a natural source, a recombinant source (i.e., a "recombinant" polypeptide is a produced by genetic engineering, e.g., introduced into a cell line on a plasmid, vector, naked DNA, etc., and expressed in the cell), or it can be produced synthetically (produced chemically or enzymatically, e.g., cleavage of a full-length corin at amino acid residue 801, e.g., using a fragment of 802–1042). The corin polypeptide can be expressed in a mammalian cell, an insect cell line, or in bacteria, e.g., as a fusion or non-fusion protein.

Preferably, corin is expressed in a cell line transformed with a corin coding sequence (e.g., a cDNA, a gene, a genomic fragment, etc.). In the latter case, the corin is present as a heterologous component of the cell; by heterologous, it is meant that the corin is coded for by a coding sequence that has been introduced by the hand of a person into the cell, e.g., by transfection, transformation, etc. Preferably, the corin is expressed at high levels in the cell (bacterial, yeast, insect, mammalian, etc.). A human corin is a preferred coding sequence. See, e.g., Seq. 1 and Seq. 2.

In a preferred aspect of the invention, the corin is provided as a cell lysate, e.g., cells transformed with human corin are lysed and the resulting lysate is used directly in the assay, i.e., a crude lysate. The crude lysate comprising the recombinant human corin can optionally be refined or enriched for human corin. For instance, membrane fractions can be isolated conventionally.

Corin can also be modulated at earlier steps in its expression pathway, e.g., modulating its transcription, mRNA stability, translation, post-translational modifications, processing (such as cleavage at the internal cleavage site), etc. Expression can be regulated using different agents, e.g., an antisense nucleic acid, a ribozyme, an aptamer, a synthetic compound, or a naturally-occurring compound.

Compounds identified in this or other manners can be useful to modulate corin activity in a cell, a tissue, a whole organism, in situ, in vitro (test tube, a solid support, etc.), in vivo, or in any desired environment. In general, a compound having such an in vitro activity will be useful in vivo to modulate a biological pathway associated with corin, e.g., to treat a pathological condition associated with the biological and cellular activities mentioned above, including bone and cardiac diseases and developmental disorders thereof, growth factor and protein maturation via serine protease activity, etc.

To treat a disease, the compound, or mixture, can be formulated into a pharmaceutical composition comprising a pharmaceutically acceptable carrier and other excipients as apparent to the skilled worker. See, e.g., Remington's Pharmaceutical Sciences, Eighteenth Edition, Mack Publishing Company, 1990. Such composition can additionally contain effective amounts of other compounds.

The present invention also relates to a method of modulating, preferably inhibiting, expression of a gene coding for a mammalian corin, comprising: contacting a cell expressing a mammalian corin of the present invention, such as a human or mouse corin, with an amount of agent, such as an antisense oligonucleotide or antisense RNA of a human or mouse corin gene, which is effective to sequence-specifically inhibit said gene. Inhibiting expression of a corin gene can inhibit the maturation of ANF, and have consequent impact on the pathways in which ANF is involved, including those mentioned above.

Sequence-specific inhibition of a gene can be accomplished conventionally using antisense nucleic acid, such as antisense oligonucleotides or RNA. For example, antisense oligonucleotides, such as phosphodiester or phosphorothioate deoxyoligonucleotides can be designed to specific regions of a corin RNA, such as to the translation initiation site, and can then be administered to cells expressing such genes in quantities effective to inhibit their expression. Generally, an antisense nucleic acid is a nucleic acid which is complementary to the sense or coding strand of a given gene, and as a result are also complementary and thus able to specifically hybridize with mRNA transcripts of the gene.

To enhance stability, the administered nucleic acid can be modified, e.g., to make it resistant to cellular enzymes, oxidation, reduction, nucleases, etc, or to enhance its uptake into cells. Any suitable modification can be used, including, e.g., phosporothioates, methylphosphonates, phosphodiester oligonucleotide linked to an acridine intercalating agent and/or a hydrophobic tail, psoralen derivatives, 2'-ribose modifications, pentose sugar derivatives, nitrogen base derivatives, etc. See, e.g., U.S. Pat. No. 5,576,208 and U.S. Pat. No. 5,744,362. See, above, for other derivatives, modifications, etc, which can be useful in the invention. In general, an antisense nucleic acid of the present invention can comprise monomers of naturally-occurring nucleotides, non-naturally-occurring nucleotides, and combinations thereof to enhance cellular uptake and/or stability.

Antisense can be administered as naked nucleic acid, complexed or encapsulated with and by other agents which facilitate its uptake into a cell, injected into cells, or any suitable delivery means in association with vectors, such as viral or adeno. Antisense gene therapy can be accomplished by any suitable method. See, e.g., Phillips, *Am. J. Cardiol*, 82:605–625, 1998; Haller et al., *Kidney Int.*, 53:1550–1558, 1998.

The present invention also relates to antibodies which specifically recognize corin. An antibody specific for corin means that the antibody recognizes a defined sequence of amino acids within or including a corin, e.g., the human and murine sequences of Seq. 2 and Seq. 3. Thus, a specific antibody will generally bind with higher affinity to an amino acid sequence, i.e., an epitope, found in Seq. 2 than to a different epitope(s), e.g., as detected and/or measured by an immunoblot assay or other conventional immunoassay. Thus, an antibody which is specific for an epitope of human corin is useful to detect the presence of the epitope in a sample, e.g., a sample of tissue containing human corin gene product, distinguishing it from samples in which the epitope is absent. Such antibodies are useful as described in Santa Cruz Biotechnology. Inc., Research Product Catalog, and can be formulated accordingly, e.g., 100 μg/ml.

Antibodies, e.g., polyclonal, monoclonal, recombinant, chimeric, humanized, can be prepared according to any desired method. See, also, screening recombinant immunoglobulin libraries (Orlandi et al., *Proc. Natl. Acad. Sci.*, 86: 3833–3837, 1989; Huse et al., *Science*, 256: 1275–1281, 1989); in vitro stimulation of lymphocyte populations; Winter and Milstein, *Nature*, 349: 293–299, 1991. For example, for the production of monoclonal antibodies, a polypeptide according to FIG. 2 or FIG. 3 can be administered to mice, goats, or rabbit subcutaneously and/or intraperitoneally, with or without adjuvant, in an amount effective to elicit an immune response. The antibodies can also be single chain or FAb fragments. The antibodies can be IgG, subtypes, IgG2a, IgG1, etc. Antibodies, and immune responses, can also be generated by administering naked DNA See, e.g., U.S. Pat. Nos. 5,703,055; 5,589,466; 5,580,859.

Corin, or fragments thereof, for use in the induction of antibodies do not need to have biological activity; however, they must have immunogenic activity. Peptides for use in the induction of corin-specific antibodies may have an amino acid sequence consisting of at least five amino acids, preferably at least 10 amino acids. Short stretches of corin amino acids, e.g., five amino acids, can be fused with those of another protein such as keyhole limpet hemocyanin, or another useful carrier, and the chimeric molecule used for antibody production.

Several different approaches, as mentioned, can be utilized to prepare antibodies specific for corin. For instance, in one approach, denatured corin from purified corin (e.g., purified by reverse-phase HPLC separation) is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In another approach, an amino acid sequence of corin, as deduced from the cDNA, is analyzed to determine regions of high immunogenicity. Polypeptides comprising these regions are synthesized and used in suitable immunization protocols to raise antibodies. Analysis to select appropriate epitopes is described by Ausubel FM et al (1989, *Current Protocols in Molecular Biology*, Vol 2. John Wiley & Sons). The optimal amino acid sequences for immunization are usually at the C-terminus, the N-terminus and those intervening, hydrophilic regions of the polypeptide which are likely to be exposed to the external environment when the protein is in its natural conformation. Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Antibodies can also be generated against any desired region, or subregion thereof, e.g, about, or comprising, amino acids 46–66; 134–259; 450–573; 268–415; 579–690; 713–801; 802–1402.

Hybridomas can also be prepared and screened using standard techniques. Hybridomas of interest are detected by screening with labeled corin to identify those fusions producing the monoclonal antibody with the desired specificity. In a typical protocol, wells of plates (FAST, Becton-Dickinson. Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled corin. 1 mg/ml. Clones producing antibodies will bind a quantity of labeled corin which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$M, preferably $10^9$ to $10^{10}$, or stronger, will typically be made by standard procedures as described in Harlow and Lane (1988) *Antibodies: A Laboratory Manual*. Cold Spring Harbor Laboratory, or Goding (1986) *Monoclonal Antibodies: Principles* and Practice, 2$^{nd}$ Ed. Academic Press N.Y.

Particular corin antibodies are useful for the diagnosis of prepathologic conditions, and chronic or acute diseases which are characterized by differences in the amount or distribution of corin. Diagnostic tests for corin include methods utilizing the antibody and a label to detect corin in human (or mouse, etc, if using mouse, etc.) body fluids, tissues or extracts of such tissues (such as in heart and cartilage tissues).

The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350: 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound corin, using either polyclonal or monoclonal antibodies specific for corin are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EC is preferred, but a competitive binding assay may be employed. These assays are described, among other places, in Maddox. Del, et al (1983) *J Exp Med* 158: 1211.

Antibodies and other ligands which bind corin can be used in various ways, including as therapeutic, diagnostic, and commercial research tools, e.g, to quantitate the levels of corin polypeptide in animals, tissues, cells, etc., to identify the cellular localization and/or distribution of it, to purify it, or a polypeptide comprising a part of it, to modulate the function of it, in Western blots, ELISA, immunoprecipitation, RIA, etc. The present invention relates to such assays, compositions and kits for performing them, etc. Utilizing these and other methods, an antibody according to the present invention can be used to detect corin polypeptide or fragments thereof in various samples, including tissue, cells, body fluid, blood, urine, cerebrospinal fluid. A method of the present invention comprises: a) contacting a ligand which binds to a peptide of Seq. 2 or Seq. 3 under conditions effective, as known in the art, to achieve binding, and b) detecting specific binding between the ligand and peptide. By specific binding, it is meant that the ligand attaches to a defined sequence of amino acids, e.g., within or including the amino acid sequence of Seq. 2 or Seq. 3 or derivatives thereof.

Native or recombinant corin can be purified by immunoaffinity chromatography using corin-specific antibodies. In general, an immunoaffinity column is constructed by covalently coupling the anti-corin antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified Ig is covalently attached to a chromatographic resin such as CnBr activated Sepharose (Pharmacia LKB Biotechnology, Piscataway, N.J.). The antibody is coupled to the resin, the resin is blocked, and the derivative resin is washed according to the manufacturer's instructions.

An immunoaffinity column is utilized in the purification of corin by preparing a fraction from cells containing corin. This preparation can be derived by solubilization of the whole cell or of a subcellular fraction obtained via differential centrifugation by the addition of detergent or by other methods well known in the art. Alternatively, soluble corin containing a signal sequence may be secreted in useful quantity into the medium in which the cells are grown.

A soluble corin-containing preparation is passed over the immunoaffinity column, and the column is washed under conditions, e.g., high ionic strength buffers in the presence of detergent, that allow the preferential absorbance of corin. Then, the column is eluted under conditions that disrupt antibody/corin binding (e.g., a buffer of pH 2–3 or a high concentration of a chaotrope such as urea or thiocyanate ion), and the corin is collected.

In addition, ligands which bind to a corin polypeptide according to the present invention, or a derivative thereof, can also be prepared, e.g., using synthetic peptide libraries or aptamers (e.g., Pitrung et al., U.S. Pat. No. 5,143,854; Geysen et al., 1987, *J. Immunol. Methods*, 102:259–274; Scott et al., 1990, *Science*, 249:386; Blackwell et al., 1990, *Science*, 250:1104; Tuerk et al., 1990, *Science*, 249: 505.)

The antibodies or derivatives thereof can also be used to inhibit expression of corin or a fragment thereof. The levels of corin polypeptide can be determined alone or in combination with other gene products. In particular, the amount (e.g., its expression level) of corin polypeptide can be compared (e.g., as a ratio) to the amounts of other polypeptides in the same or different sample, e.g., actin. In general, reagents which are specific for corin can be used in diagnostic and/or forensic studies according to any desired method, e.g., as U.S. Pat. Nos. 5,397,712; 5,434,050; 5,429, 947.

The present invention also relates to a corin polypeptide, prepared according to a desired method, e.g., as disclosed in U.S. Pat. No. 5,434,050. A labeled polypeptide can be used, e.g., in binding assays, such as to identify substances that bind or attach to corin, to track the movement of corin in a cell, in an in vitro, in vivo, or in situ system, etc.

A nucleic acid, polypeptide, antibody, corin, ligand etc., according to the present invention can be isolated. The term "isolated" means that the material is in a form in which it is not found in its original environment, e.g., more concentrated, more purified, separated from component, etc. An isolated nucleic acid includes, e.g., a nucleic acid having the sequence of corin separated from the chromosomal DNA found in a living animal. This nucleic acid can be part of a vector or inserted into a chromosome (by specific gene-targeting or by random integration at a position other than its normal position) and still be isolated in that it is not in a form which it is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a corin or a corin knock-out. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,22,778; Gordon et al., Proc. Natl. Acad. Sci., 77:7380–7384 (1980); Palmiter et al., Cell, 41:343–345 (1985); Palmiter et al., Ann. Rev. Genet., 20:465–499 (1986); Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993. A nucleic acid according to the present invention can be introduced into any non-human mammal, including a mouse (Hogan et al., 1986, in Manipulating the Mouse Embryo: A Laboratory Manual, Cold Spring Harbor Laboratory, Cold Spring Harbor, N.Y.), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., 1987, Trends in Biotech. 5:20–24; and DePamphilis et al., 1988, BioTechniques. 6:662–680. In addition, e.g., custom transgenic rat and mouse production is commercially available. These transgenic animals are useful animals models to test for corin function, as food for a snake, as genetic markers to detect strain origin, etc. Such transgenic animals can further comprise other transgenes or knock-outs thereof (e.g., in other serine proteases, natriuretic peptides, etc.).

Transgenic animals comprising multiple copies of the corin gene, the corin gene driven by strong promoters, or corin knockouts, can be useful as animal models for hypertension, renal disease, and cardiac disease. See, e.g., Steinhelper et al., Hypertension, 16:301–307, 1990; John et al., Am. J. Physiol., 27 1:R109–R114, 1996.

The present invention thus relates to a transgenic animal, such as a rodent, a mouse, or a rat, comprising cells which contain a recombinant corin gene integrated into a chromosome of said cell at the native corin gene locus, said recombinant corin gene comprising a nucleotide coding sequence which codes for a recombinant corin polypeptide comprising at least one amino acid whose identity and/or position is not naturally-occurring in said native corin gene. Such a recombinant gene can be produced by homologous recombination, e.g., between a human corin and the corin gene of the host animal at its native locus.

The present invention also relates to a transgenic animal, such as a mouse or a rat, comprising cells which contain at least one functionally disrupted recombinant corin gene at a chromosomal corin gene locus, wherein said disruption prevents functional expression of the corin polypeptide coded for by the corin gene. Functional inactivation or disruption refers, e.g., to a partial or complete reduction of the expression of at least a portion of a polypeptide encoded by an endogenous serine protease gene of a single cell, selected cells, or all of the cells of a mammal. Such reduction can result in concomitant reduction in pro-ANF-converting enzyme activity, causing a decrease in physiologically-active ANF. The term "knockout" is a synonym for functional inactivation of the gene.

In one embodiment, a gene targeting strategy is utilized that facilitates the introduction of a desired nucleotide sequence into a corin gene. The gene targeting strategy preferably utilizes double reciprocal recombination and a positive selectable marker to assist in the insertion of the nucleotide sequence into a target nucleic acid. The target nucleic acid is preferably a gene, more preferably a gene at its particular chromosomal locus. The desired nucleotide sequence is inserted into the gene in such a way that the gene is functionally disrupted, i.e., its expression is partially or completely reduced.

Modification of the corin gene at is chromosomal locus can be accomplished according to any suitable method, such as homologous recombination. The latter can be used to disrupt the corin gene, introduce a gene mutation into the corin gene, insert or delete DNA, etc. Selection and use of sequences effective for homologous recombination is described, e.g., in Deng and Capecchi. Mol. Cell. Bio., 12:3365–3371. 1992: Bollag et al., Annu. Rev. Genet., 23:199–225, 1989; Waldman and Liskay, Mol. Cell. Bio., 8:5350–5357, 1988; Rubinstein et al., Nucl. Acid Res., 21:2613–2617, 1993; WO94/23049; WO95/14377.

The corin gene can be completely functionally disrupted, e.g., by deleting 5' regions of the gene. Alternatively, specific regions of corin can be modified. For instance, the catalytic domain at about amino acid positions 802–1042 in the human corin gene, or corresponding positions in the mouse gene, can be genetically altered by recombination to produce a corin with modified activity, including null activity, increased activity, reduced activity.

Generally, the nucleic acids, polypeptides, antibodies, etc, of the present invention can be prepared and used as described in. U.S. Pat. Nos. 5,501,969, 5,506,133, 5,441, 870; WO 90/00607; WO 91/15582.

For other aspects of the nucleic acids, polypeptides, antibodies, etc., reference is made to standard textbooks of molecular biology, protein science, and immunology. See, e.g., Davis et al. (1986), Basic Methods in Molecular Biology, Elsevier Sciences Publishing, Inc., New York; Hames et al. (1985), Nucleic Acid Hybridization, IL. Press, Molecular Cloning, Sambrook et al.; Current Protocols in Molecular Biology, Edited by F. M. Ausubel et al., John Wiley & Sons, Inc; Current Protocols in Human Genetics, Edited by Nicholas C. Dracopoli et al., John Wiley & Sons, Inc.; Current Protocols in Protein Science; Edited by John E. Coligan et al., John Wiley & Sons, Inc.; Current Protocols in Immunolog; Edited by John E. Coligan et al., John Wiley & Sons, Inc.

EXAMPLES

Isolation of Human Corin cDNA Clones

A partial EST sequence was identified based on analysis of Incyte EST database for novel serine protease cDNAs. The clone (307474) was ordered from Incyte. A 2.1 kb EcoRI-XhoI fragment from the clone was used to screen a human heart cDNA library (Clontech). Phagemid 14b2, which contains a 3.8 kb insert, was obtained from one positive phage clone by in vivo exision. Oligo primers which derived from phagemid 14b2 were used to further clone 5=-end cDNA sequence by 5' RACE, using Marathon-ready human heart cDNA (Clontech) as templates. The PCR products were cloned into pCRII vector (Invitrogen) and sequenced. The full-length (i.e., having an initiation codon and a termination codon) human corin cDNA sequence was obtained by compiling sequences obtained from 5'-RACE and phagemid using GCG DNA sequence analysis package.

Oligo Primers Used in 5' RACE

PrWY109: 5'-CAGTTGGTTTGAACAAGTGCAGGG-3' (SEQ ID NO:5)
PrWY110: 5'-TGCAAGGAGGGATACGCTCGCCTG-3' (SEQ ID NO:6)
PRWY111: 5'-AATCCCAAGAACAGACTCACAGCG-3' (SEQ ID NO:7)
PRWY118: 5'-CGGGTCACAGAGAGAGCTACCACC-3' (SEQ ID NO:8)
PRWY119: 5'-GGTCTCCTTCTTGACATGAATCTG-3' (SEQ ID NO:9)
5'-AACAAAACGATCCTTGGAGGTCGGACGAGT-3' (SEQ ID NO:10)

Northern Analysis

The 2.1 kb-EcoRI-XhoI fragment of Incyte clone 307474 was labeled by $^{32}$P-dCTP using a random primer labeling kit (Boehringer). Human Multiple Tissue Northern Blot I, Human Multiple Tissue Northern Blot II, Human Muscle Northern Blot filters (Clontech) were hybridized with the labeled human corin cDNA probe. The Northern hybridization was carried out overnight at 42EC with 40% formamide, 5× Denhardts solution, 6×SSC, 100 μg/ml salmon sperm DNA, 0.1% SDS. The filters were washed with 0.2×SSC, 0.1% SDS at 60EC, and exposed to Fuji imaging plates.

Cloning of Mouse Corin cDNA

Mouse corin cDNA clones were isolated by a PCR-based strategy. A mouse heart cDNA library was purchased from Clontech and used as templates for PCR amplification (30 cycles of 1.5-min annealing at 55EC, 1.5-min extension at 72EC, and 1-min denaturation at 94EC). The sequences of PCR primers are based on the human corin cDNA sequences. Primers used for amplification of the mouse cDNA include:

Cor09: 5'-TCTTCTGTGTACTAAACAAGACTG-3' (SEQ ID NO:11)
Cor12: 5'-AGGCCCCAGGACTTTGGAAAAGCA-3' (SEQ ID NO:12)
Cor02: 5'-ACAGTGGCCTGAAGACACAGATTG-3' (SEQ ID NO:13)
Prwy128: 5'-ACAGAGCATCGCTGCGGGGACGGG-3' (SEQ ID NO:14)

DNA fragments from the PCR reactions were cloned into the pCRII vector. Plasmid clones that were derived from independent PCR reactions were used for further sequencing. Mouse and human corin cDNAs share over 85% sequence identities.

In situ Hybridization

RT-PCR-mRNA samples were isolated from Hec-1-A, U2-OS, SK-LMS-1, and AN3-CA cells using a commercial RNA preparation kit (Oligtex Direct mRNA Mini Kits, QIAGEN). First strand cDNAs were synthesized using SuperScript II RNase-reverse transcriptase (Life Technologies). Human corin specific oligonucleotide primers (sense primer: 5'-AACAAAAGGATCC-TTGGAGGTCGGACGAGT-3' (SEQ ID NO:15) and antisense primer: 5'-CGGAGCCCCATGAAGTTAATCCA-3') (SEQ ID NO:16) were used to amplify a 630-bp fragment of corin cDNA between nucleotides 2475 and 3105. Oligonucleotide primers TFR1 (5'-GTCAATGTCC-CAAACGTCACCAGA-3') (SEQ ID NO:17) and TFR2 (5'-ATTTCGGGAATGCTGAGAAAACAGACAGA-3') (SEQ ID NO:18), derived from the human glyceraldehydes-3-phosphate dehydrogenase (GAPDH) gene, were used as an internal quantification control. PCR reactions were performed with a thermal cycler (Perkin-Elmer, model 480). PCR products were separated on 1% agarose gels and visualized by ethidium bromide staining.

In Situ Hybridization—Mouse adult heart and embryonic tissue sections were deparaffinized in xylene, rehydrated and fixed in 4% paraformaldehyde. The tissues were digested with proteinase K (20 mg/ml), then treated with triethanolamine acetic anhydride and dehydrated. An 800-bp mouse corin cDNA fragment from the coding region was cloned into pCRII (Invitrogen) in vivo orientations to yield plasmids pM11 and pM41. The plasmids were linearized by HindIII digestion. Sense and antisense probes were synthesized using T7 RNA polymerase (T7/SP6 transcription kit, Boehringer Mannheim) and labeled with [33P]UTP (Amersham). The hybridization was carried out as described (14). The slides were dehydrated and dipped in Kodak NTB-2 emulsion and exposed for 4 weeks in light-tight boxes at 4° C. Photographic development was carried out in a Kodak D-19 developer. The slides were stained with hemotoxin and eoisin and analyzed using both light- and dark-field optics of a Zeiss microscope.

Fluorescent In Situ Hybridization (FISH) Analysis—P1 phage clones containing the human corin gene were isolated by filter hybridization using a human corin cDNA as the probe. One clone was confirmed by DNA sequencing using a primer from human corin cDNA. The DNA fragment from this P1 phage was labeled with digoxigenin-dUTP. The labeled probe was combined with sheared human DNA and hybridized to metaphase chromosomes derived from PHA-stimulated peripheral blood lymphocytes in a solution containing 50% formamide, 10% dextran sulfate and 2×SSC. Hybridization signals were detected by fluorescent-labeled antidigoxigenin antibodies and counter-staining with DAPI (4,6-diaminoidino-2-phenylindole). A total of 80 metaphase cells were analyzed of which 74 cells exhibited specific labeling.

Homology Model of the Protease Domain of Corin—A model of the corin protease domain (amino acids 802–1042) was built based on the structure of bovine chymotrypsinogen Å at 1.8 Å resolution (15,16), using the Homology program (Insight II, 1995, MSI, San Diego, Calif.). Rotamers were used for non-identical side-chain replacements (16). Coordinates for the loop insertions were extracted from the Brookhaven protein data bank (17). The model was refined by energy minimization using the AMBER force field (Discover 95.0), with a distance-dependent dielectric constant. The minimization used the steepest descents and conjugate gradient methods: first for the loops only where insertions and deletions occurred, then side-chains, and a final round of minimization keeping the Ca atoms fixed. The residues of corin (His843, Asp892 and Ser985) corresponding to the catalytic triad of the template structure were also held fixed.

Biological Activity of Corin

Several different cell lines were produced by conventional methods to assay for the biological activity of corin, 293 cells were cotransfected with pro-ANF and corin expressing plasmids. Two additional cell lines were created by cotransfecting 293 cells with a pro-ANF expressing plasmid and a hepsin or prothrombin expressing plasmid. Only the cells expressing corin converted pro-ANF to ANF as demonstrated by Western blot using antibodies to ANF.

Another experiment was conducted in which conditioned media containing pro-ANF was contacted with a cells expressing recombinant corin polypeptide. Again, pro-ANF was converted to ANF. Control cells expressing hepsin or prothrombin had no effect on pro-ANF.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents, publications, nucleic acids having sequence identification numbers, etc., cited above and in the figures are hereby incorporated in their entirety by reference, including the following nucleic acid fragments from the Unigene, PubEST, and GenbBank databases: Hs.62794 (AA126468 [1686098], AA126648 [1686206], AA625395 [2537780], AA046682 [1524579], AA249850 [1881137], and AA046793 [1524691]), and Hs.71798 (AA147031 [1716421]); Hs.121626 (AA771958). Hs.1657 (M69297), and Hs.47712 (AA203291), g1231787; g1312726; g1337948; and g942724.

From the foregoing description, one skilled in the art can easily ascertain the essential characteristics of this invention, and without departing from the spirit and scope thereof, can make various changes and modifications of the invention to adapt it to various usage and conditions.

What is claimed is:

1. An isolated nucleic acid comprising a nucleotide sequence coding for amino acid 1 to amino acid 1042 as set forth in SEQ ID NO:2.

2. An isolated nucleic acid comprising nucleotide sequence set forth in SEQ ID NO:1.

3. An isolated nucleic acid comprising the nucleotide sequence set forth in SEQ ID NO:1 from position 95 through position 3221 and encoding a corin polypeptide having serine protease activity.

4. An isolated nucleic acid of claim 1, wherein the nucleotide sequence is operably linked to an expression control sequence.

5. An isolated nucleic acid of claim 1, wherein the nucleic acid codes for said polypeptide without interruption.

6. A vector comprising a nucleic acid of claim 1.

7. A transformed host cell containing a nucleic acid of claim 1.

8. A method of expressing in transformed host cells, a human corin coded for by a nucleic acid, comprising:
   culturing transformed host cells containing a nucleic acid of claim 1 under conditions effective to express the polypeptide.

9. A method of claim 8, wherein said host cells are mammalian.

10. A method of claim 8, further comprising isolating the membrane fraction of said host cells comprising said polypeptide.

11. An isolated full-length human corin polypeptide having serine protease activity comprising amino acid 1 to amino acid 1042 as set forth in SEQ ID NO:2.

12. An isolated full-length human corin polypeptide having serine protease activity and which is coded for by nucleotide positions 95–3221 of the nucleotide sequence set forth in SEQ ID NO:1.

13. An isolated polypeptide produced by a method of claim 8.

14. A method of identifying an inhibitor of the serine protease catalytic activity of a human corin polypeptide comprising:
   reacting, in the presence of a test compound, a full-length human corin polypeptide having serine protease activity and comprising the sequence of amino acids from 1 to 1042 of SEQ ID NO:2, and a substrate for the corin serine protease, under conditions effective for said polypeptide to cleave said substrate;
   detecting said cleavage; and,
   identifying whether the test compound inhibits said serine protease activity by comparing the amount of cleavage in the presence and absence of the test compound.

15. A method of claim 14 wherein said corin polypeptide is encoded by the nucleotide sequence set forth in SEQ ID NO:1.

16. A method of claim 14, wherein the substrate is pro-ANF.

17. A method of claim 14, wherein said substrate is chromogenic, and cleavage of said substrate results in the appearance of a detectable color.

* * * * *

UNITED STATES PATENT AND TRADEMARK OFFICE
CERTIFICATE OF CORRECTION

PATENT NO. : 6,806,075 B1
DATED : October 19, 2004
INVENTOR(S) : Morser et al.

It is certified that error appears in the above-identified patent and that said Letters Patent is hereby corrected as shown below:

<u>Title page,</u>
Item [75], Inventor, change "John Michael Morser, San Francisco" to
-- Michael John Morser, San Francisco --.

Signed and Sealed this

Nineteenth Day of April, 2005

JON W. DUDAS
*Director of the United States Patent and Trademark Office*